US010854320B2

(12) United States Patent
Fuhrmann

(10) Patent No.: US 10,854,320 B2
(45) Date of Patent: Dec. 1, 2020

(54) MESSAGING SYSTEM FOR INITIATING EVENT BASED WORKFLOW

(71) Applicant: Epic Systems Corporation, Verona, WI (US)

(72) Inventor: David Fuhrmann, Verona, WI (US)

(73) Assignee: EPIC SYSTEMS CORPORATION, Verona, WI (US)

(*) Notice: Subject to any disclaimer, the term of this patent is extended or adjusted under 35 U.S.C. 154(b) by 573 days.

(21) Appl. No.: 15/049,949

(22) Filed: Feb. 22, 2016

(65) Prior Publication Data

US 2016/0173424 A1 Jun. 16, 2016

Related U.S. Application Data

(63) Continuation of application No. 13/835,406, filed on Mar. 15, 2013, now abandoned, which is a
(Continued)

(51) Int. Cl.
*G16H 10/60* (2018.01)
*G16H 80/00* (2018.01)
(Continued)

(52) U.S. Cl.
CPC .......... *G16H 10/60* (2018.01); *G06F 3/0481* (2013.01); *G16H 80/00* (2018.01); *H04L 51/046* (2013.01); *H04L 51/28* (2013.01); *H04L 51/36* (2013.01); *G06F 19/324* (2013.01); *G06F 19/328* (2013.01); *G06F 19/34* (2013.01);
(Continued)

(58) Field of Classification Search
CPC ........ G16H 10/60; G16H 80/00; G16H 40/67; G16H 30/20; G16H 20/30; G16H 70/60; G16H 20/10; G16H 40/63; G16H 20/60; G16H 40/20; G16H 15/00; G06F 19/322; G06F 19/3481; G06F 19/3418; G06F 19/328; G06F 19/3475; G06F 19/3456; G06F 19/324; G06F 3/0481; G06F 19/34; H04L 51/046; H04L 51/36; H04L 51/28;
(Continued)

(56) References Cited

U.S. PATENT DOCUMENTS 8,626,524 B1 * 1/2014 Koehl .................... H04L 51/08
705/2
2008/0082366 A1 * 4/2008 Miller ................... G06Q 10/10
705/3
(Continued)

*Primary Examiner* — Christopher L Gilligan
(74) *Attorney, Agent, or Firm* — Quarles & Brady LLP

(57) ABSTRACT

The disclosure includes a method and system for initiating at least one workflow associated with a patient, the system enabling users to create electronic messages, the method comprising the steps of presenting an electronic message via a display wherein the electronic message includes at least fields, associating the displayed electronic message with a first patient, receiving a general event descriptor entered by a system user via an interface in one of the message fields where the general event descriptor can be used to identify at least one workflow being requested by the user, obtaining the general event descriptor from the field, identifying a workflow associated with the general event descriptor and associated with the first patient and transmitting an electronic message to at least one entity that is capable of handling the workflow being requested by the user.

20 Claims, 11 Drawing Sheets

Related U.S. Application Data continuation-in-part of application No. 12/987,252, filed on Jan. 10, 2011, now Pat. No. 8,812,599.

(51) Int. Cl.

| | | |
|---|---|---|
| *H04L 12/58* | (2006.01) | |
| *G06Q 50/24* | (2012.01) | |
| *G16H 15/00* | (2018.01) | |
| *G06F 3/0481* | (2013.01) | |
| *G06F 19/00* | (2018.01) | |
| *G06Q 50/22* | (2018.01) | |
| *G06Q 50/00* | (2012.01) | |
| *G16H 40/20* | (2018.01) | |
| *G16H 20/30* | (2018.01) | |
| *G16H 70/60* | (2018.01) | |
| *G16H 20/10* | (2018.01) | |
| *G16H 40/63* | (2018.01) | |
| *G16H 20/60* | (2018.01) | |

(52) U.S. Cl.
CPC ...... *G06F 19/3418* (2013.01); *G06F 19/3456* (2013.01); *G06F 19/3475* (2013.01); *G06F 19/3481* (2013.01); *G06Q 50/01* (2013.01); *G06Q 50/22* (2013.01); *G06Q 50/24* (2013.01); *G16H 15/00* (2018.01); *G16H 20/10* (2018.01); *G16H 20/30* (2018.01); *G16H 20/60* (2018.01); *G16H 40/20* (2018.01); *G16H 40/63* (2018.01); *G16H 70/60* (2018.01); *H04L 51/14* (2013.01); *H04L 51/26* (2013.01)

(58) Field of Classification Search
CPC ......... H04L 51/14; H04L 51/26; G06Q 10/10; G06Q 50/24; G06Q 50/22; G06Q 50/01
See application file for complete search history.

(56) References Cited

U.S. PATENT DOCUMENTS

| | | | | |
|---|---|---|---|---|
| 2008/0306759 | A1* | 12/2008 | Ilkin | G06Q 10/10 705/2 |
| 2009/0132586 | A1* | 5/2009 | Napora | G16H 40/20 |
| 2009/0147940 | A1* | 6/2009 | Graves | H04M 3/42365 379/208.01 |
| 2011/0191122 | A1* | 8/2011 | Kharraz Tavakol | G06Q 10/10 705/3 |
| 2011/0295961 | A1* | 12/2011 | Wilkes | G06Q 50/24 709/206 |

* cited by examiner

MESSAGING SYSTEM FOR INITIATING EVENT BASED WORKFLOW

CROSS-REFERENCE TO RELATED APPLICATIONS

This application is a continuation of U.S. patent application Ser. No. 13/835,406 which is titled "Messaging System For Initiating Event Based Workflow" which was filed Mar. 15, 2013, which is a continuation in part of U.S. patent application Ser. No. 12/987,252 which is titled "Networked Inbox" and which was filed on Jan. 10, 2011, all of which are incorporated herein by reference in their entirety.

STATEMENT REGARDING FEDERALLY SPONSORED RESEARCH OR DEVELOPMENT

Not applicable.

BACKGROUND OF THE INVENTION

1. Field of the Invention

The present invention relates to electronic messaging between two entities and specifically to sending messages from one entity to another that leverages information stored by one of the entities and contextual information associated with the message to identify an intended unknown message recipient.

2. Description of the Related Art

In the medical industry it is often the case that patients see many different physicians, medical assistants, nurses, specialists, etc., in the course of receiving services. Thus, for instance, a patient may initially consult a primary care physician about an ailment, be referred out for tests and imaging activities to one or several different institutions and be referred to one or more specialists, for additional services. Here, in order to provide optimal service for a patient, all caregivers that provide services to a patient need to be able to easily communicate amongst themselves. One way for caregivers to communicate between themselves is via an electronic messaging system.

Typical electronic messaging systems allow one user to send a message to a second user by addressing the message to a specified address associated with the second user. For example, in an e-mail system, each individual user has their own specific address. The e-mail address is usually in the form of: username@domainname. Thus, a user of GMAIL.COM with a user name of "john.smith" would have an e-mail address of "john.smith@gmail.com".

It is known that an administrator can establish a single e-mail address that can be routed to a number of different recipients by an e-mail server. For example, a company might have a single customer service e-mail address such as customer.service@company.com. A server associated with the customer service e-mail address forwards messages received at the customer service address to a number of different e-mail accounts of employees responsible for monitoring customer service questions. The message is thus distributed to several customer service employees indiscriminately. The company can then use the customer service e-mail address in its product literature so that questions from customers or the general public can be handled without concerns about changes at the company itself: employee turn over, vacations, etc. Furthermore, the actual recipients of the messages can remain generally unknown to the sender at the time the sender sends the electronic message.

While the single e-mail address concept works well for routing messages to a group of intended recipients, unfortunately there is no easy way to use a similar single e-mail address to route a message to one of a plurality of possible recipients. For instance, in a case where an ear, nose and throat (ENT) specialist intends to route a message to a patient's primary care physician (PCP) and does not know the PCP's name or e-mail address, there is no easy way for the ENT specialist to address an e-mail to a single PCP address and have the messaging system deliver the message to the patient's PCP. Similarly, where a patient's PCP intends to route a message to the patient's ENT specialist and does not know who the specialist is or the specialist's e-mail address, currently there is no way for the PCP to address a message to a single address and have the message automatically delivered to the patient's ENT specialist. This problem is exacerbated in cases where patient's are serviced by many different physicians and across unaffiliated entities where familiarity between all caregivers and addressing conventions is highly unlikely.

BRIEF SUMMARY OF THE INVENTION

It has been recognized that even when a message sender does not have enough information or access to information usable to identify an intended recipient of a message and/or the recipient's e-mail address, a system can be set up that can use a short descriptor of the recipient and additional contextual information associated with a message to identify an intended recipient. Here, the short recipient descriptor alone is insufficient for the system to identify the intended recipient address but the short recipient descriptor along with the contextual information is sufficient to identify the recipient address.

For instance, where an ENT specialist is working in a patient's medical record chart when the specialist decides to send an e-mail to the patient's PCP, the specialist may be able to simply fill in PCP in the "To" field of an e-mail template. When PCP is typed into the "To" field, a server may be programmed to identify a PCP associated with the patient that is associated with the currently viewed chart, identify an electronic messaging system address for the PCP and fill in the PCP address automatically. In this case, "PCP" is the short recipient descriptor and the patient identifier operates as the contextual information used along with the recipient descriptor to automatically identify the recipient's address.

In other embodiments, after an e-mail targeting PCP is composed, prior to transmission, a patient identifier may be added to the e-mail in some fashion that identifies the patient associated with the chart accessed when the e-mail was composed. Here, the patient identifier again serves as contextual information associated with the e-mail being composed. Upon receiving the e-mail with the patient identifier, receiving e-mail server may then use the PCP identifier and the patient identifier to identify a PCP associated with the patient, identify an address for the PCP and forward the e-mail message to the intended PCP.

In still other embodiments, after PCP is entered in a "To" e-mail field while a patient chart is being examined by an ENT specialist and prior to transmitting the e-mail, a pre-e-mail may automatically be transmitted to at least a subset of servers including the PCP short recipient identifier and a patient identifier associated with the patient's chart being viewed when PCP was entered in the "To" field. In response, each receiving e-mail server may use the PCP identifier and patient identifier to attempt to identify the patient's PCP.

Where a server identifies the patient's PCP address, the server automatically transmits the PCP address back to the specialist's e-mail server. The specialist's e-mail server then can either automatically fill in the PCP address in the "To" field, associate the PCP address with the "To" field or provide an option for the specialist to select the PCP address to fill in the "To" field.

In other embodiments, where a specialist fills "PCP" into a "To" field and then transmits an e-mail prior to the PCP address being resolved, if a receiving e-mail server cannot resolve a unique intended recipient using the PCP descriptor and other contextual information, the server may respond with either an error message or, in the case where two or a small subset of possible intended recipients is resolvable, may provide a list of possible intended recipients for the specialist to choose from. When a list of possible intended recipients is presented and one is selected, the e-mail is then delivered to the selected recipient.

In still other embodiments it is contemplated that contextual information may be gleaned from some part of an e-mail as opposed to being obtained from a currently viewed patient's chart. For instance, it may be required practice for a physician to enter a unique patient identifier in a "Re" line of an e-mail when communicating with another physician about a patient. In this case, the patient identifier (i.e., the contextual information) required to identify a patient's PCP may be gleaned from the "Re" line of an e-mail and used to resolve an intended recipient. Contextual information may be gleaned from other locations as well. In other embodiments patient information may be added to an attachment or the like associated with and transmitted with other e-mail information.

Some embodiments include a computer-implemented electronic messaging method comprising the steps of receiving an electronic message at a first system, the electronic message comprising a caregiver type, obtaining contextual information associated with the electronic message at the first system, using the caregiver type and the contextual information to identify an intended caregiver recipient address for an intended caregiver recipient for the electronic message and providing the intended caregiver recipient address to facilitate delivery of the electronic message to the intended caregiver recipient.

In some cases the step of obtaining contextual information associated with the electronic message includes obtaining a patient identifier identifying a patient associated with the electronic message. In some cases the step of obtaining a patient identifier includes obtaining the patient identifier from a patient chart.

In some cases the step of obtaining the patient identifier from a patient chart includes obtaining the patient identifier from a patient chart most recently accessed by a caregiver composing the electronic message. In some cases the step of obtaining a patient identifier includes gleaning the identifier from information in the electronic message.

In some cases the step of using the caregiver type and the contextual information to identify an intended caregiver recipient address for an intended caregiver recipient for the electronic message includes the steps of associating a patient chart with the electronic message, identifying a caregiver of the caregiver type indicated in the patient chart and identifying an electronic address for the identified caregiver. In some cases the step of receiving an electronic message at a first system includes composing the electronic message at a second system where the electronic message specifies the caregiver type and includes the contextual information and transmitting the electronic message to the first system. In some cases the step of receiving an electronic message at a first system includes receiving the electronic message as the message is entered and prior to transmission of the electronic message. In some cases the electronic message is composed using the first system.

In some cases the electronic message is composed using a second system separate from the first system and wherein the step of receiving the electronic message includes receiving the electronic message from the second system at the first system. In some cases the caregiver type is selected from the group consisting of: doctor, pediatrician, primary care physician, radiologist, specialist, pharmacist, and surgeon. In some cases the caregiver type is a generic type.

In some cases the step of providing the intended caregiver recipient address includes automatically inserting the intended caregiver recipient address in an address field in the electronic message. In some cases the step of providing the intended caregiver recipient address includes presenting the intended caregiver recipient address for selection as a target address for the electronic message.

Other embodiments include a networked messaging system comprising a first medical record system comprising patient records and caregiver records and a first computer system communicatively linked to the first medical record system, the first computer system programmed to perform the steps of receiving an electronic message, the electronic message comprising a caregiver type, obtaining contextual information associated with the electronic message, using the caregiver type and the contextual information to identify an intended caregiver recipient address for an intended caregiver recipient for the electronic message and providing the intended caregiver recipient address to facilitate delivery of the electronic message to the intended caregiver recipient.

In some cases the system is programmed to perform the step of obtaining contextual information associated with the electronic message by obtaining a patient identifier identifying a patient associated with the electronic message. In some cases the system is programmed to perform the step of obtaining a patient identifier by obtaining the patient identifier from a patient chart. In some cases the system is programmed to perform the step of obtaining the patient identifier from a patient chart by obtaining the patient identifier from a patient chart most recently accessed by a caregiver composing the electronic message.

In some cases the system is programmed to perform the step of obtaining a patient identifier by gleaning the identifier from information in the electronic message. In some cases the system is programmed to perform the step of using the caregiver type and the contextual information to identify an intended caregiver recipient address for an intended caregiver recipient for the electronic message by associating a patient chart with the electronic message, identifying a caregiver of the caregiver type indicated in the patient chart and identifying an electronic address for the identified caregiver. In some cases the system is programmed to perform the step of receiving an electronic message at a first system by receiving the electronic message from a second system used to compose the electronic message where the electronic message specifies the caregiver type and includes the contextual information.

In some cases the system is programmed to perform the step of receiving an electronic message at a first system by receiving the electronic message as the message is entered and prior to transmission of the electronic message. In some cases the electronic message is composed using the first system. In some cases the electronic message is composed using a second system separate from the first system and wherein the step of receiving the electronic message includes receiving the electronic message from the second system at the first system. In some cases the caregiver type is selected from the group consisting of: doctor, pediatrician, primary care physician, radiologist, specialist, pharmacist, and surgeon.

In some cases the step of providing the intended caregiver recipient address includes automatically inserting the intended caregiver recipient address in an address field in the electronic message. In some cases wherein the step of providing the intended caregiver recipient address includes presenting the intended caregiver recipient address for selection as a target address for the electronic message.

Still other embodiments include a computer-implemented electronic messaging method, the method comprising the steps of receiving a general recipient descriptor at a first system where the general recipient descriptor is associated with an electronic message and the general recipient descriptor is descriptive of a plurality of different possible intended message recipients, obtaining contextual information associated with the electronic message, using the general recipient descriptor and the contextual information to identify an intended message recipient address; and providing the intended message recipient address to facilitate delivery of the electronic message to the intended message recipient.

Unless indicated otherwise, the above described systems and processes that are concerned with helping a caregiver direct e-mails to intended recipients in a simplified and streamlined fashion will be referred to herein generally as "recipient based" systems or processes.

It has also been recognized that, in addition to recipient based systems and processes, an e-mail system may be configured as an event based system where an e-mail can be used to start one or more workflows or events including but not limited to medical procedures, medical or health consults, imaging procedures, follow-up care, etc., in an intuitive and streamlined fashion. For instance, in some embodiments of the present disclosure, when a caregiver intends to order a specific event for a patient such as an MRI, the e-mail server system may enable the caregiver to simply type "MRI" into an e-mail address or target field to indicate that an MRI event should be initiated for the patient. When the e-mail is sent (e.g., the caregiver selects a "send" icon), the e-mail along with additional contextual patient information may be sent to a system e-mail server or other server which can use the descriptor and contextual information to identify a requested patient specific workflow and may start an MRI process or a series of procedures or workflows required by a medical entity or organization to complete an MRI process for the patient.

For instance, an MRI process for a healthcare organization or entity may include using content related to a patient's medical chart and specifically recent information related to the activities associated with the caregiver requesting the MRI process to identify an MRI procedure to be performed, identifying a healthcare entity capable of performing the MRI procedure to be performed that is available in a time frame needed by the requesting caregiver and that is conveniently located for the patient to use and scheduling an MRI session for the patient to complete the process.

In at least some embodiments an event based e-mail (e.g., MRI) may cause a string of e-mails to facilitate all sub-processes that comprise the event. For instance, in the above MRI example, a first healthcare entity may perform scheduling for a plurality of different imaging entities, one of the imaging entities may be a second entity and the second entity may use a third entity to perform a pre-MRI consultation. In this case, when an e-mail addressed to MRI is received by an e-mail system, the e-mail may initially be directed to the first entity to identify a conveniently located and available entity capable of performing the MRI procedure. In response to receiving the initial MRI e-mail, the first entity may send a round of e-mails or messages of another type to multiple imaging entities including the second entity indicating the procedure to be performed as well as any time requirements starting with imaging entities proximate the location of the requesting caregiver or the patient's home address resulting in a subset of available and convenient entities capable of completing the MRI procedure. The second and other imaging entities may reply to the received messages by indicating capabilities and availability causing the first entity to schedule the MRI to be completed by the second entity. Once the MRI is scheduled for the second entity, the second entity may send another e-mail or other electronic message to the third entity to start a pre-MRI consultation sub-process.

As another instance, when a patient's primary care physician intends to order a consult with a specialist, the physician may simply address an e-mail to "consult" and an e-mail server receiving the e-mail may be programmed to automatically start a specialist consultation process or series of procedures or sub-processes required by a medical entity or organization to complete the consultation process.

As another instance, a physician may address an initial e-mail to "surgery". Here, the system receiving the e-mail would glean information from a patient's medical record chart and use that information to kick off a detailed event or set of events associated with the surgery request. For instance, a patient may require surgery to replace a portion of the patient's skull removed during a prior surgical procedure to allow unrestricted swelling associated with brain trauma. In this case the system may be programmed to determine the type of surgery required or intended by the physician based on recent information added by the physician to the patient's chart and cause an entire process to be kicked off including identifying a convenient, capable and available entity or a preferred physician (e.g., the surgeon that removed the portion of the skull) to perform the surgery, scheduling the surgery, schedule a pre-surgery consult and schedule post surgery activities including time at a skilled nursing facility (SNF) needed for recovery including rehabilitation.

In some cases, a system server is programmed to, upon identifying a likely requested event using a descriptor and a set of contextual information, seek immediate confirmation from a requesting caregiver via an warning notice that the workflow identified by the system is the intended or is a suitable workflow. For instance, it may be that a receiving entity has a specific preferred sequence of MRI processes that it performs to generate diagnostic information needed for a specific ailment. A physician, however, may have a different preferred set of MRI processes. By sending an immediate event confirmation message (e.g., in the form of a new window specifying the event to perform and an "accept" icon) to a physician, unintended or less than optimal ordered activities may be avoided. An additional benefit of the confirmation feature is that caregivers will likely adopt the system more readily as the caregivers will be more comfortable initiating a process that has a final confirmation step prior to initiation. For instance, entering "surgery" or "MRI" in an e-mail address may be disconcerting, at least initially, if a physician is unclear what occurs when the e-mail is sent. This may be particularly important in cases where a patient's chart or information there from will be sent to an entity that is not directly affiliated with the entity that a caregiver is associated with.

Some embodiments consistent with at least some aspects of the present disclosure include a computer-implemented electronic messaging method for initiating at least one workflow associated with a patient, the messaging system enabling users to create electronic messages, the method comprising the steps of providing a processor programmed to perform the steps of, presenting an electronic message template as an electronic message via a display wherein the electronic message includes fields, the fields including at least one target field in which a user may enter information usable to identify an intended recipient of the electronic message, associating the displayed electronic message with a first patient, receiving a general event descriptor entered by a system user via an interface in one of the message fields where the general event descriptor can be used to identify at least one workflow being requested by the user, obtaining the general event descriptor from the one of the message fields, identifying a workflow associated with the general event descriptor and the first patient and transmitting an electronic message to at least one entity that is capable of handling the workflow being requested by the user to initiate the workflow being requested.

In some cases the method further includes the step of accessing contextual information associated with the first patient, the step of identifying a workflow associated with the general event descriptor and associated with the first patient including using the contextual information and the general event descriptor to identify the workflow being requested. In some embodiments patient charts including patient medical records are stored in a database and include at least a first patient's chart associated with the first patient, the step of accessing contextual information including accessing information in the first patient's chart. In some cases the method further includes the steps of providing a rule set that correlates general event descriptors with contextual information types, the step of accessing contextual information including using the rule set to identify contextual information types correlated with the received general event descriptor and identifying information of the identified contextual information type in the first patient chart, the identified information being first patient contextual information.

In some cases the method further includes the step of associating at least a portion of the first patient contextual information with the electronic message prior to transmission to the at least one entity that is capable of handling the workflow being requested by the user. In some embodiments the step of associating at least a portion of the first patient contextual information with the electronic message includes adding the at least a portion of the first patient contextual information to at least one field in the electronic message. In some embodiments the step of associating at least a portion of the first patient contextual information with the electronic message includes providing a contextual information access key along with the electronic message which can be used to access the at least a portion of the first patient contextual information. In some cases the method further includes the step of, after identifying a workflow associated with the general event descriptor and associated with the first patient, providing a notice to the user via the display warning that the workflow has been requested.

In some cases the step of providing a notice occurs prior to the step of transmitting an electronic message to at least one entity that is capable of handling the workflow being requested by the user. In some embodiments the notice includes a confirmation tool that can be selected via the interface to confirm that the workflow is being requested, the method further including receiving a confirmation via the confirmation tool and transmitting the electronic message to the at least one entity that is capable of handling the workflow being requested after receiving the confirmation. In some cases the method further includes the step of, prior to transmitting the electronic message to at least one entity capable of handling the workflow being requested, receiving the electronic message at a server, the method further including creating a second electronic message including the notice and transmitting the second electronic message back to the user to view on the display.

In some embodiments the steps of creating a second electronic message including the notice and transmitting the second electronic message back to the user to view on the display occur prior to the step of transmitting the electronic message to at least one entity capable for handling the workflow being requested. In some embodiments the steps of identifying a workflow associated with the general event descriptor and associated with the first patient and providing a notice to the user via the display warning that the workflow has been requested occur prior to the user initiating transmission of the electronic message. In some cases the step of providing a notice includes automatically adding information to the electronic message that comprises a specified workflow request.

In some cases wherein transmission of the electronic message including the notice comprises confirmation that the requested workflow is intended. In some embodiments wherein the general event descriptor indicates at least one of a medical test workflow and a medical procedure workflow. In some embodiments wherein the general event descriptor indicates a consultation. In some embodiments wherein the general event descriptor indicates a request for extended patient care. In some embodiments wherein the step of receiving the general event descriptor includes receiving the general event descriptor in the target field of the electronic message.

Some embodiments include a computer-implemented electronic messaging method for initiating at least one workflow associated with a patient, the method enabling users to create electronic messages, the method comprising the steps of providing a database including patient charts, the patient charts including at least a first patient's chart, each patient chart including patient medical records for an associated patient, presenting an electronic message template as an electronic message via a display wherein the electronic message includes fields, the fields including at least one target field in which a user may enter information usable to identify an intended recipient of the electronic message, associating the displayed electronic message with the first patient, receiving a general event descriptor entered by a system user via an interface in at least one of the fields, obtaining the general event descriptor from the at least one of the fields, accessing the database to obtain contextual information from the first patient's chart, the contextual information obtained from the first patient's chart being first patient contextual information, using the contextual information and the general event descriptor to identify a workflow being requested and transmitting an electronic message to at least one entity that is capable of handling the workflow being requested by the user.

In some cases the method further includes the steps of using the contextual information and the general event descriptor to identify the at least one entity that is capable of handling the workflow being requested. In some cases the method further includes the step of automatically adding at least a portion of the first patient contextual information to the electronic message prior to the step of transmitting. In some cases the first patient contextual information automatically added to the electronic message specifies the workflow being requested in more detail than the general event descriptor.

In some cases the method further includes the step of automatically adding information to the electronic message prior to the step of transmitting that indicates the identity of the at least one entity that is capable of handling the workflow being requested. In some embodiments the step of receiving the general event descriptor includes receiving the general event descriptor in the target field of the electronic message.

Some embodiments include a computer-implemented electronic messaging method for initiating at least one workflow associated with a patient, the method enabling users to create electronic messages, the method comprising the steps of presenting an electronic message template as an electronic message via a display wherein the electronic message includes fields, the fields including at least one target field in which a user may enter information usable to identify an intended recipient of the electronic message, associating the displayed electronic message with a first patient, receiving a general event descriptor entered by a system user via an interface in at least one of the message fields where the general event descriptor can be used to identify at least one workflow being requested by the user, obtaining the general event descriptor from the message field, identifying a workflow associated with the general event descriptor and associated with the first patient, providing a warning notice to the user via the display indicating the workflow and transmitting an electronic message to at least one entity that is capable of handling the workflow being requested by the user.

In some embodiments the step of providing a notice includes providing the notice prior to transmitting the electronic message. In some cases the step of providing a notice includes automatically adding information to the electronic message while the message is displayed to the user on the display where the message specifies detail of the identified workflow. In some embodiments the step of providing a notice includes, after the user selects a send button to transmit the electronic message, generating and transmitting a separate electronic message to the user to be displayed on the display screen. In some cases the step of receiving the general event descriptor includes receiving the general event descriptor in the target field of the electronic message.

Other embodiments include a computer system for initiating at least one workflow associated with a patient, the computer system enabling users to create electronic messages, the system comprising a user interface including a display and at least one user input device, a processor programmed to perform the steps of presenting an electronic message template as an electronic message via a display wherein the electronic message includes fields, the fields including at least one target field in which a user may enter information usable to identify an intended recipient of the electronic message, receiving a general event descriptor entered by a system user in at least one of the message fields via the input device where the general event descriptor can be used to identify at least one workflow being requested by the user, obtaining the general event descriptor from the at least one of the fields, identifying a workflow associated with the general event descriptor and associated with the first patient and transmitting an electronic message to at least one entity that is capable of handling the workflow being requested by the user.

Some embodiments include an computer system for initiating at least one workflow associated with a patient, the computer system enabling users to create electronic messages, the system comprising a user interface including a display and at least one user input device, a database including patient charts, the patient charts including at least a first patient's chart, each patient chart including patient medical records for an associated patient, a processor linked to the database and the user interface and programmed to perform the steps of presenting an electronic message template as an electronic message via a display wherein the electronic message includes fields, the fields including at least one target field in which a user may enter information usable to identify an intended recipient of the electronic message, associating the displayed electronic message with the first patient, receiving a general event descriptor entered by a system user via an input device in at least one of the message fields, obtaining the general event descriptor from the at least one of the message fields, accessing the database to obtain contextual information from the first patient's chart, the contextual information obtained from the first patient's chart being first patient contextual information, using the contextual information and the general event descriptor to identify a workflow being requested and transmitting an electronic message to at least one entity that is capable of handling the workflow being requested by the user.

Still other embodiments include an computer system for initiating at least one workflow associated with a patient, the computer system enabling users to create electronic messages, the system comprising a user interface including a display and at least one user input device, a processor linked to the user interface and programmed to perform the steps of presenting an electronic message template as an electronic message via a display wherein the electronic message includes fields, the fields including at least one target field in which a user may enter information usable to identify an intended recipient of the electronic message, associating the displayed electronic message with a first patient, receiving a general event descriptor entered by a system user via an interface in at least one of the message fields where the general event descriptor can be used to identify at least one workflow being requested by the user, obtaining the general event descriptor from the at least one of the message fields, identifying a workflow associated with the general event descriptor and associated with the first patient, providing a notice to the user via the display warning indicating the workflow and transmitting an electronic message to at least one entity that is capable of handling the workflow being requested by the user.

Other embodiments include a computer system for initiating at least one workflow associated with a patient using an electronic messaging system wherein each electronic message includes message fields including at least one target field, the system comprising a processor programmed to perform the steps of receiving an electronic message including at least one general event descriptor in at least one of the message fields, identifying the general event descriptor, identifying a workflow associated with the general event descriptor, identifying an entity capable of handling the identified workflow and transmitting an electronic message to the entity capable of handling the workflow to initiate the workflow.

In some cases the method further includes the steps of, after identifying the workflow, transmitting a notice to the user that initiated the received electronic message indicating the identified workflow. In some cases the notice includes a confirmation tool usable by the user to indicate the user's intent to initiate the workflow, the processor further programmed to perform the steps of monitoring the confirmation tool to identify user confirmation of the workflow. In some embodiments the workflow ceases when the user fails to confirm intent to request the workflow.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE INVENTION

Figure 1:
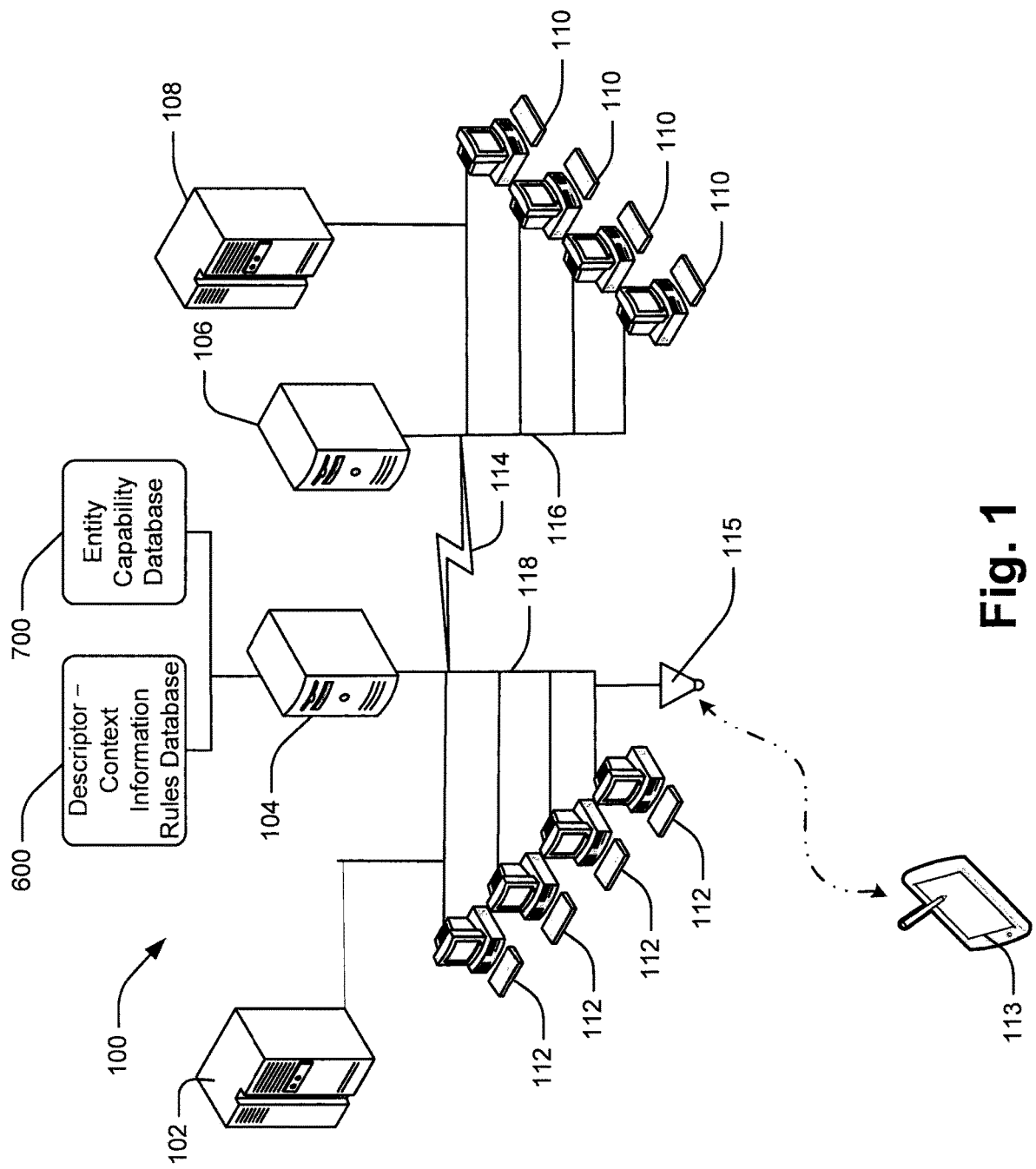
FIG. 1 is an exemplary embodiment of a possible messaging system in accordance with one embodiment of the present invention.

A. Recipient Based Messaging Systems and Methods

The present invention is directed to a method of communicating messages from one entity to another wherein the first entity does not know the actual identity and/or electronic address of an intended recipient. The messaging may be useful in any situation in which one party refers messages to another such as occur in medical or healthcare, legal, insurance, shipping, inventory management, and other similar fields. For simplicity, the following description uses an example of sending electronic messages between two medical institutions including St. Mary's Hospital ("St. Mary's") and a local healthcare cooperative ("LHC").

In one embodiment, St. Mary's Hospital and LHC have established an inter-institution messaging network 100. The messaging network 100 may connect two or more electronic medical records ("EMR") systems 102 and 108 by a communication network 114, 116, 118. Each institution's EMR system 102 and 108 contains information regarding a patient including contact information, patient medical histories, schedules, visit information, doctors associated with the patient, prescriptions, treatments, emergency contact information, payment information, medical images, and lab results.

The communications network may be implemented using an industry standard network, including the internet 114 that links together local or wide area networks 116 and 118 associated with related medical entities, that permits electronic transmission of information from one server to another. In the case of electronic messages between two distinct institutions, the messaging network 100 may comprise at least one messaging or e-mail server 104 and 106 at each of the institutions. The communications network 114, if implemented on the Internet, may be implemented using a virtual private network wherein the two messaging servers are treated as if they are on a private network.

Referring still to FIG. 1, devices 110 and 112 are associated with LHC's and St. Mary's e-mail servers 104 and 106, respectively. Devices 110 and 112 are shown as desktop computers but may be any type of interface devices such as laptops, wireless phones or smart palm type devices, pad type devices, etc. Each interface device can be used to compose and send electronic messages to other devices 110 or 112. In FIG. 1, an exemplary wireless pad computing device 113 is shown linking to network 118 via a wireless access point 115.

Where a message is sent from one device to another device associated with the same entity (e.g., St. Mary's), the message is routed from the sending device to the e-mail server associated with the entity and out to the target device in most cases without transmission through network 114. For instance, a message from a first device 112 to a second device 112 associated with St. Mary's in FIG. 1 would be routed through server 104 without passing through network 114.

Where a message is sent from one device 112 associated with St. Mary's to another device 110 associated with LCH, the message is routed to St. Mary's e-mail server 104, through network 114 to server 106 which in turn routes the message to the intended recipient address. Here, information in the electronic message assists the sending messaging server 104 to determine where and how to send the electronic message to the receiving messaging server 106. A messaging server 104 or 106 may act as both a sending messaging server and a receiving messaging server.

Hereafter, unless indicated otherwise, the phrase "internal message" will be used to refer to a message sent from one device to another device where the sending and receiving devices are served by a single e-mail server (e.g., 104 or 106). Similarly, the phrase "external message" will be used to refer to a message between devices that are served by different e-mail servers. For instance, a message between one device 112 and another device 110 that are served by servers 104 and 106, respectively, would be an external message.

In one exemplary scenario, a physician using a computer 112 at St. Mary's desires to send an external message to another physician or healthcare professional using a computer 110 at LHC. For example, a first physician enters information regarding a patient visit into St. Mary's EMR system 102 using his or her computer 112 regarding an emergency room visit. The physician then desires to send some or all of the information to the patient's PCP at a local family care clinic run by LHC. It will be appreciated that LHC may be running a different EMR system 108 than St. Mary's (i.e., EMR system 102). It will be further appreciated that even if the two institutions have an EMR system sold by the same vendor, the particular instances and implementations may be separate with separate databases, servers, and patient records. Accordingly, the first physician may not have ready access to either the name of the primary care physician or the electronic message address for the physician.

In accordance with the present invention, the physician at St. Mary's may compose an electronic message using St. Mary's EMR system 102 or e-mail system 104 using computer 112. The electronic message may include an address and a patient identifier. Additional information may be included with an electronic message such as a subject, a return address, a message body, certain header and routing information, and part or all of a patient medical record. The electronic message of the instant invention may be implemented using either common electronic messaging schemes including e-mail (e.g., smtp and imap) or a custom messaging system.

Figure 2A:
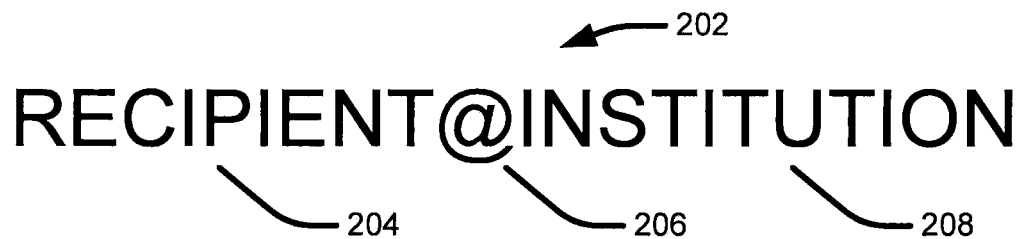
FIGS. 2A-C show exemplary embodiments of possible recipient descriptor addressing schemes.

With reference to FIG. 2A, an address for an electronic message may be in a form 202 of: recipient@institution. For instance, if the physician knows the name of the patient's primary care physician is Dr. John Smith, the physician could compose the message with an address: john.smith@LHC. In this case, the address is composed of the recipient designation 204 and the institution identifier 208 separated by token 206 indicated by the "@".

Figure 2B:
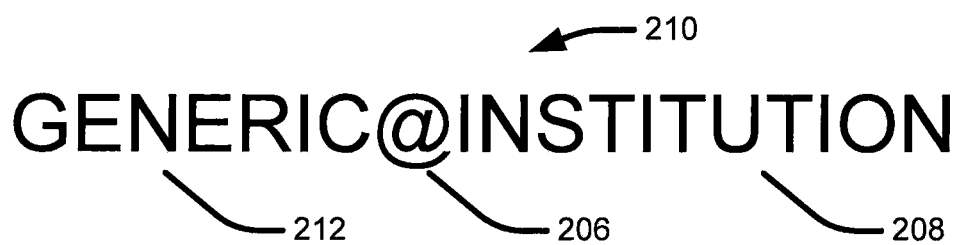
Figure 2C:
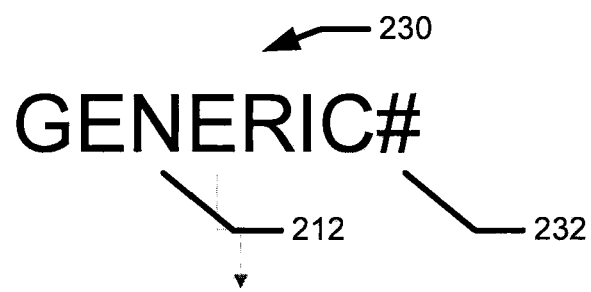

However, when a physician does not know the name of a patient's PCP or does not know the format of an address in the LCH system, as is typically the case for electronic messages sent between two separate institutions, the physician using the electronic messaging system 100 of the present invention can address the message using a generic or general descriptor or identifier 212 and an institution identifier 208 separated by a token 206 as shown in FIG. 2B. For instance, an exemplary descriptor of this type may be PCP@LHC. In this case "PCP" is short for "primary care physician." Similarly, if, instead of the primary care physician, the physician wanted to send a message to the patient's surgeon, the physician could address the message as: surgeon@LHC. Accordingly, the messaging system allows the physician to address electronic messages using one of a set of short descriptive generic "caregiver" type identifiers.

In addition, the addressing function can also be shorthand for intra-institution communications or internal messages. For example, even if the physician could determine a patient's PCP—as either provided by an EMR system or by a patient—the physician can avoid looking up the PCP's address and simply address the electronic message using either generic identifier 212 and institution identifier 208 (e.g., PCP@stmarys) or, even more simply, using generic identifier 212 (e.g., PCP). In the second example, the institution identifier 208, "@stmarys", is implied since the physician is sending the message internally. In this case, the address comprises only the caregiver type descriptor.

Similarly, even if a patient's primary care physician is not part of the St. Mary's EMR system 102, a physician may still be able to address the electronic message by its generic identifier 212 (e.g., as "PCP"). In this case, St. Mary's EMR system 102 may have previously recorded PCP information associated with a patient. This information may include both the name of the patient's PCP and an associated institution. Accordingly, if the EMR system 102 indicates that the patient has a "PCP" at LHC, messages addressed to PCP will be rerouted to "PCP@LHC". This functionality is described in further detail below with respect to the routing of electronic messages using information from the EMR system.

In at least some embodiments, an electronic message also includes a patient identifier. In one embodiment, the patient identifier is simply a numeric or alpha-numeric key that uniquely identifies a patient record in an EMR system. However, under the scenario above, St. Mary's EMR system 102 and LHC's EMR system 108 may not have common, unique patient record identifiers. In this case, one alternative is to create a token that can be included with the electronic message that will be recognized by a receiving messaging server. In this embodiment, a patient may provide the token that can be read and stored by the sender's EMR system. For example, the patient may carry a card with the token represented by a bar code or magnetic strip. The token is read by the physician's system and the token is stored within the electronic message sent from St. Mary's and will be used to identify the patient at LHC's messaging server 106, as further discussed below.

In the case that neither a common, unique identifier or token is available, the patient identifier may include a sufficient amount of contextual identifying information within the electronic message so that the EMR system at the receiving institution can correctly and uniquely identify the patient. For example, the electronic message may include one or more of the following: first name, last name, date of birth, last four digits of a social security number, mother's maiden name, number of children, and place of birth. There are many possible combinations of information that may be successfully used as a patient identifier. This information can be retrieved from a sending party's EMR system and incorporated into the electronic message as part of the body, the header, or as an attachment. For instance, in at least some embodiments, when a specialist is using an EMR system to view a patient chart and decides to send an e-mail to the patient's PCP upon opening up an e-mail application to compose the message, the system may automatically glean patient identifier information (e.g., a patient identifier) from the currently opened patient chart and add that information to an e-mail field. As another instance, when a specialist is composing an e-mail to a PCP as indicated by entry of "PCP" in an e-mail "To" field, the system may automatically identify the last ten patient charts viewed by the specialist and provide a list of ten patient identifiers for selection by the specialist. Here, upon selection of a patient from the list, a patient identifier would be added to an appropriate e-mail field.

The electronic message may also include a body that contains the message to be delivered. The body can be free form text typed by the sender. It can also be structured text based on a field or fields in the sender's EMR system. In the latter case, for example, the body of the electronic message can be an automated report filled in using information saved in the EMR system by the physician. For example, an Emergency Room physician may send an electronic message comprising a discharge report to a patient's PCP. The discharge report can be a template or form document in which the information regarding the visit can be automatically completed by using values stored in St. Mary's EMR system 102.

In addition, the electronic message may include part or all of an electronic medical record. This information may be copied as text into the body of the electronic message. It can also be attached to the electronic message as a file attachment. It may also be attached as an electronic link. The electronic link provides information for a communications protocol whereby the receiving system can remotely retrieve information from the sender's EMR system.

In the context of an EMR system, it is contemplated that the functions for sending and receiving messages in an electronic messaging system 120 of the present invention may be incorporated directly into the EMR system. In this case, the electronic messaging system 100 has ready access to the patient's medical record information while the messaging is being prepared and before it is sent.

In at least some embodiments, when a sender finishes an electronic message and sends it, the message is provided to the sender's messaging server 104. The sender's messaging server 104 is responsible for routing the message to the recipient's messaging server via the communications network 114. The process of routing may involve obtaining the external address of the recipient's messaging server 106, preparing the electronic message for transmission across the communications network 114, encrypting the electronic message, and actually sending the electronic message.

In the case of an "external" message, (i.e., a message addressed to an entity outside the sender's EMR system 102), the sender's messaging server 104 must determine the address of the external entity by examining the address in the e-mail. In the above example addressed to "PCP@LHC" the sender's messaging server 104 must first determine where and what institution identifier 208, "LHC," means. The sender's messaging server 104 or the sender's EMR system 102 may be programmed so that an "institution" named "LHC" points at the server address of the local health cooperative. This information may be indexed by the name "LHC." The server address may be an internet protocol address ("IP" address) or other uniform resource indicator ("URI") that includes protocol, IP address, and port number and other communication information. The server address could also be an internet domain such as "localhealthcooperative.org." If the institution is found, the message is routed using an appropriate communications protocol. If no institution is found, then the messaging server may return the message to the sender. The return message may include information that no such institution is found. Alternatively, or in addition to returning the message to the sender, the message could be sent to an assistant or other specialist at the sender's institution for proper addressing information.

In addition, as noted above, another embodiment of the present invention might have a situation in which the sender addresses a message without an institution identifier 208 (e.g., "PCP"), where the sender's EMR system 102 has a record in a patient chart indicating that the generic identifier "PCP" is, in fact, an external entity. In this case, upon retrieving the destination information for "PCP" from the patient record for the patient matching the patient identifier, the message is rerouted by the sending messaging server 104 using the proper institution. For example, if the EMR system 102 identifies that a PCP is at LHC, then the message is not delivered internally, but the address is changed to "PCP@LHC" and resent. Alternatively, if the EMR system 102 has the complete address for the primary care physician, Dr. John Smith having an address john.smith@localhealthcooperative.org, then the message can be sent directly to that address avoiding additional processing by both the sending EMR system 102 and receiving EMR system 108.

With respect to both internal messaging and the situation in which a sending EMR system 102 contains some or all of the relevant contact information, the sender user interface can implement the appropriate addressing queries directly. For example, as the Emergency Room physician types "PCP" into the address field of a message composition screen on computer 112, the user interface software can search the EMR system 102 for any corresponding record. As discussed above, a message may be composed in the context of a patient record and, therefore, the messaging system 100 may have ready access to information in the EMR system 102. Accordingly, the user interface software can pass both the generic identifier "PCP" and a patient identifier directly to the EMR system 102 in order to retrieve the corresponding results. If the EMR system 102 returns the destination address of john.smith@localhealthcooperative.org, for example, then the address of "PCP" can be replaced with john.smith@localhealthcooperative.org.

In the context of an "external" message, the sending messaging server 104 is responsible for sending the electronic message across the communications network 114 to the receiving messaging server 106. Upon receiving the message, the receiving messaging server 106 will first determine the proper recipient of the electronic message. It will be appreciated that "PCP" or "doctor" or "surgeon" and other caregiver types potentially identify a large number of users of the receiving institution's EMR system 108, but only a few or perhaps one will be associated with a particular patient. Accordingly, a system of the present invention may select from among all the possible recipients only those that correspond to the patient identifier. In other words, the combination of caregiver type and the patient identifier will select a subset of all possible caregivers at a receiving institution. As a result, a select group of all users of the corresponding caregiver type is set as the actual intended recipient(s). So, for example, if there are 1000 doctors that are in the category of "primary care physician" at LHC, and the patient has only one primary care physician, then the electronic message addressed to PCP@LHC for this patient will be delivered only to the one designated primary care physician, not every primary care physician.

In one embodiment, a receiving messaging server 106 will query the EMR system 108 for the address information of the caregiver corresponding to both the patient identifier and the caregiver type. In the case that the patient identifier is a token or a common, unique identifier, the patient record may be retrieved directly from the EMR system 108. In the case that the electronic message only includes patient information, the receiving messaging server 108 uses some or all of the supplied patient information in the electronic message to identify a single patient in the receiving messaging server's 106 EMR system 108. In any case, if a patient record is successfully retrieved and a corresponding caregiver is found, then the message is routed, by the receiving messaging server 106, to the intended recipient's computer 110.

In a possible embodiment, the receiving messaging server 106 may also return to the sending messaging server 104 an acknowledgement that the message was successfully received. The acknowledgement may also include the address information of the intended recipient. The sending messaging server 104 then may use the information in the acknowledgement to update its own EMR system 102. In this case, any future messages to the patient's primary care physician, for example, can be routed directly to the PCP without requiring additional processing by the receiving messaging server 106. The acknowledgement itself may also be sent directly to the sender or saved to the EMR system 102 for future reference.

If, however, the receiving messaging server 106 cannot find either a corresponding patient or a corresponding caregiver, an undeliverable message may be returned to the sending messaging system 104. Similarly, if the receiving messaging server 106 is unable to identify a single patient from the receiving messaging server's EMR system 108, the receiving messaging server 106 may also return an undeliverable message. In the latter case, it will be understood that both the sending and receiving institutions may want to guard a patient's privacy and, thus, it may be inappropriate to send a message to more than one patient. The sending messaging server 104 can forward the undeliverable message to the sender for additional action. In some embodiments, the undeliverable message may include which information failed: i.e., "no such patient," "no such caregiver," "patient no longer member of this institution," etc.

Alternatively, instead of or in addition to returning an undeliverable message, the receiving messaging server 106 may also query its own EMR system 108 for additional information. For example, if the EMR system 108 contains a record for the patient but notes that the primary care physician is at another institution, then the receiving messaging server 106 can return such information to the sending messaging server 106. In addition, the receiving messaging server could reroute the electronic message to the correct institution using the messaging system.

The system of the present invention also contemplates more complicated routing routines for use with generic caregiver types. The generic caregiver types could include things like "specialist" or "surgeon" or "nurse." In the case of specialist, any particular hospital or medical system could have hundreds of types of specialists: cardiac, pulmonary, ENT, endocrinology, anesthesiology, podiatry, etc. Such naming conventions may be inconsistent as between institutions and the address information may not be readily apparent or accessible for a user attempting to send a message. A system in accordance with the present invention can use information present in the associated medical records to correctly select an intended message recipient from among all of the specialists. For example, if the patient were admitted to St. Mary's Emergency room for complications related to a patient's diabetes, the Emergency Room physician may want to send a message to the patient's endocrinologist at LHC. However, instead of writing "endocrinologist@LHC" the emergency room physician can simply type an address such as "specialist@LHC." In this case, the electronic message further contains information regarding the admission to the emergency room regarding diabetes. Such information could include the fact of the visit, vital medical information, the problem, and the medicine or treatments prescribed, and other customary information. The receiving messaging server 106 then could use the "problem," or such other appropriate indicator, identified as "diabetes complications" to select a patient's diabetes specialist from among all of a patient's specialists.

In another embodiment, the caregiver type may be associated with more than one recipient. For example, in the endocrinologist example above, the specialist for endocrinology may also be associated with the patient's diabetes nurse educator, nutritionist, and primary care physician. In this case, when the receiving messaging server 106 queries the EMR system 108 for the diabetes specialist, more than one recipient is returned. The message may then be forwarded to all of the recipients in at least some embodiments.

Similarly, in the case of a surgery or other similar event, a message directed to "surgeon" or "surgery" and referencing a particular operation may be delivered to all or a subset of the people associated with that surgery, e.g., a surgeon, a surgical assistant, an anesthesiologist, etc.

In still other cases, a list of possible patient specific possible intended recipients may be automatically provided for a physician to choose from. For instance, when "specialist" is entered in an address field, the inventive system may identify a list of five different specialists associated with a patient that is associated with the message being composed. Here the list of five specialists is provided, and one or more may be chosen as intended recipients. Upon selection, recipient addresses are used to replace the "specialist" designation.

A similar result is possible for ordering labs, medical images or prescriptions. In the case of a pharmacy, a physician can use an electronic message to deliver prescriptions or instructions to the patient's designated pharmacy. In this case, addressing a message to "pharmacy" or "pharmacy@LHC" can route message information to the patient's designated pharmacist. In some cases, if special approval is needed, the receiving messaging system could determine that, not only should the designated pharmacy/pharmacist receive the message, but that the patient's PCP should receive a message in order to maintain proper updates to the primary care physician's EMR system.

In another embodiment of the present invention, the electronic message may also include part or all of a patient's electronic medical record from the sender's EMR system 102. The receiving messaging server 106 can then incorporate that information into its own EMR system 108. For example, if the Emergency Room physician attached a visit record from the emergency room visit to an electronic message, the receiving messaging server 106 may desire to incorporate information regarding that visit into its own EMR system 108. It could, for example, record information about the fact of the visit, the date of the visit, the problems, the doctor, the treatment and any corresponding prescriptions directly into its own electronic medical records. In one embodiment, this information will be included automatically. In another embodiment, only certain portions of the medical record will be incorporated into the receiving messaging system's 106 EMR system 108.

Furthermore, the electronic message may include additional attachments or documents that the receiving messaging system may wish to retain in its own medical records system. For example, if the sending institution is a radiology clinic and the electronic message is sent to the primary care physician, the electronic message may include copies of x-rays or MRI scans. In one embodiment, the electronic message could identify such attachments accordingly, and the receiving messaging system may automatically store such documents to the corresponding location in its own EMR system. In addition, in order to prevent duplication of images, the receiving messaging system could strip the attachments from the electronic message before forwarding the messages to the intended recipients and include, rather than a complete image file, a link to the location in the EMR system.

In another embodiment, the electronic message, its contents and attachments, or any combination thereof may be encrypted by the sending messaging server. In order to protect patient privacy and patient medical and health information, the electronic message may be encrypted using one or more forms of known encryption methods. In one possible embodiment, the sending and receiving messaging servers have a shared encryption key. If a messaging server can send messages to more than one other messaging server, the messaging server may store different encryption keys for each of the messaging servers with which it can communicate. The sending messaging server then, before sending the electronic message, can encrypt the electronic message using the shared encryption key. The information is then transmitted to the receiving messaging server. The receiving messaging server then can retrieve the shared encryption key associated with the sending messaging server and decrypts the electronic message.

Each messaging server 104 or 106 may be a general purpose computer server. The computer server includes a receiving means for receiving an electronic message and a sending means for forwarding the electronic message to its intended recipient or recipients. The receiving means comprises a processor and memory unit for executing a software program or algorithm to receive an electronic message. The receiving means may further include a network connection for connecting to the communications network. The networking connection may be a network card that is connected to the communications network. In the alternative, the receiving means may comprise a communicative link to a database system or EMR system for receiving a message sent internally. The software is programmed to accept incoming electronic message. The software may be an industry standard e-mail software server running an industry standard e-mail protocol such as SMTP or IMAP. Alternatively, the software program may be a messaging system integrated with the EMR system for exchanging messages. This software program may be implemented so as to monitor the communications network for traffic on a specific port.

The sending means comprises a processor and memory unit for executing a software program or algorithm to send an electronic message. It may also further comprise a network connection for the purpose of sending electronic message external to the messaging system. The network connection may be a networking card connected to the communications network. In the alternative, the sending means may comprise a communicative link to a database system or EMR system for storing a message sent internally. The software may be an industry standard e-mail software server running an industry standard e-mail protocol such as SMTP or IMAP. Alternatively, the software program may be a messaging system integrated with the EMR system for exchanging messages. This software program may be implemented so as to monitor the communications network for traffic on a specific port.

The messaging system further comprises a patient record retrieving means. The patient record retrieving means comprises a processor, memory unit and a communicative link to a disk. The disk may be located locally on the messaging system or at a remote database or EMR system. Accordingly, the communicative link may be a physical connection with the messaging system, a network connection, or a high speed device connection (firewire, USB, or similar). The disk stores one or more patient records. The messaging system is programmed to retrieve patient records from the disk using standard database operations or disk operations. For instance, if the disk has a relational database, the messaging system is programmed to query the database using the patient identifier to retrieve the corresponding patient record.

The messaging system further comprises a caregiver record retrieving means. The caregiver record retrieving means comprises a processor, a memory unit and a communicative link to a disk. The disk may be located locally on the messaging system or at a remote database or EMR system. Accordingly, the communicative link may be a physical connection with the messaging system, a network connection, or a high speed device connection (firewire, USB, or similar). The disk stores one or more caregiver records. As with the patient record retrieving means, the messaging system is programmed to retrieve caregiver records from the disk using standard database operations or disk operations. For instance, if the disk has a relational database, the messaging system is programmed to query the database using the patient identifier and the caregiver type to retrieve the corresponding patient record.

Figure 3:
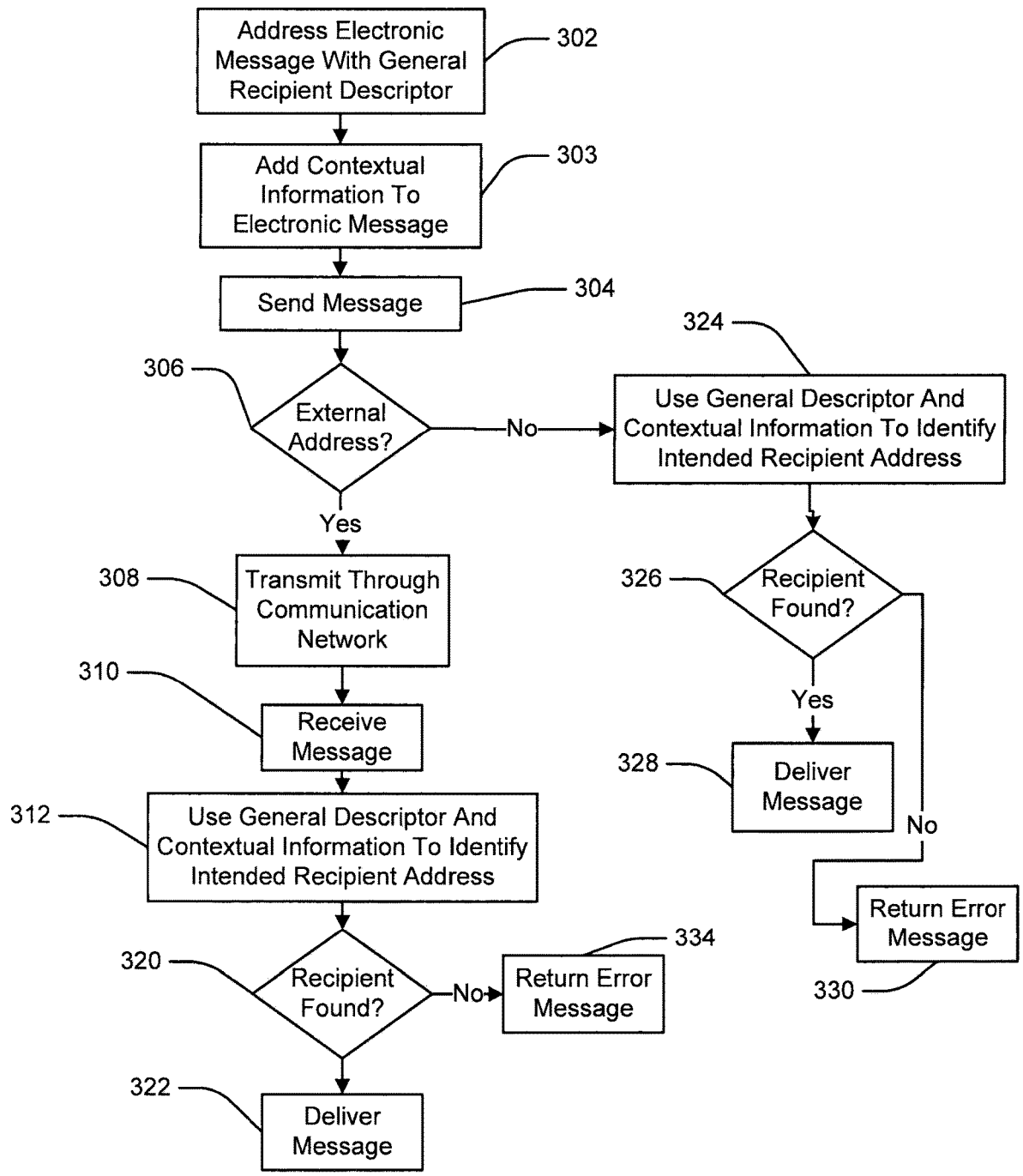
FIG. 3 is a flowchart showing one possible workflow for sending and receiving an electronic message in accordance with one embodiment of the present invention.

Referring now to FIG. 3, an exemplary flow chart showing one work flow for sending and receiving electronic messages in accordance with at least one embodiment of the present invention is illustrated. Referring also to FIG. 1, at block 302, a caregiver may compose an electronic message using one of the messaging servers 104 in which the caregiver addresses the intended recipient using one of the general recipient descriptors (e.g., PCP). At block 303 the messaging server 104 automatically adds contextual information to the electronic message. Here, again, for example, the contextual information may include a patient identifier or some other type of information that may be useful in resolving which of several PCPs to which the electronic message should be transmitted. In the alternative, the message may already include contextual information. At block 304 the caregiver selects a send icon or the like to send the electronic message to a recipient.

Referring still to FIGS. 1 and 3, at decision block 306, the messaging server 104 determines whether or not the message is targeted to an external recipient or an internal recipient serviced by server 104. Where the message is intended for an internal recipient, control passes to block 324 where messaging server 104 uses the general descriptor and contextual information to identify an intended recipient address. At block 326, if no recipient is found, control passes to block 330 where an error message is returned to the physician indicating that no intended recipient address has been identified. At block 326, when a recipient is found, control passes to block 328 where the electronic message is delivered to an electronic address associated with the intended recipient.

Referring once again to decision block 306, where the message is intended for an external recipient, control passes to block 308 where the message is transmitted through a communication network (see 114 in FIG. 1) to a second messaging server 106 associated with the external address. After the message is received at the second messaging server 106 at block 310, control passes to block 312 where the receiving server uses the general descriptor and contextual information to identify an intended recipient address. Once an intended recipient address has been identified at block 320, control passes to block 322 where the message is delivered to the intended recipient via the address. Where no recipient is identified by block 320, control passes to block 334 where an error message is returned.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. For example, the invention is to cover any case where a general recipient descriptor is associated by a message composer (e.g., a caregiver) with an electronic message and contextual information is associated with the message where the general recipient descriptor and contextual information are then used to automatically resolve one or a small subset of intended message recipients irrespective of which of several servers in a networked system performs the resolving process. For instance, as indicated above, a server used to compose an e-mail may resolve an intended recipient if the server has sufficient information. As another instance, a messaging server receiving an electronic message including the general recipient descriptor and contextual information may resolve the intended recipient. EMR systems may help resolve intended recipients as well.

As another example, in at least some embodiments it is contemplated that a first server used to compose a message may communicate with a second server after a general recipient descriptor is provided (e.g., entered in an e-mail address field) and before the electronic message is sent or even finally composed where the second server can resolve an intended recipient and provide the recipient's address back to the first server to be used during subsequent transmission of the electronic message. Here, for instance, after "PCP@LHC" is specified by a physician, a first server may glean patient identifier information and send a pre-e-mail to the LHC EMR system to retrieve an intended recipient address. The LHC EMR system uses the general recipient descriptor PCP and patient identifier to identify an address for the patient's PCP which is transmitted back to the first server. The first server can either present the intended recipient address to the physician for selection or automatically replace the "PCP@LHC" descriptor with the intended recipient address.

Moreover, in some cases an affirmation step may be required where, after a general recipient descriptor is entered into an address field and prior to transmitting a message intended for a recipient, the inventive system uses the descriptor and contextual information associated with the message to identify a likely intended recipient and presents the recipient for selection by the message composer as opposed to automatically replacing the descriptor with the recipient's address. Here, the affirmation requirement is an added step which should minimize the possibility of a message being inadvertently transmitted to an incorrect or unintended recipient.

In still other cases, when a message composer selects a send icon to send a message to a recipient identified via a general descriptor (e.g., PCP), the system may first resolve a likely intended recipient and provide a recipient identifier (e.g., a caregiver's name) for selection prior to transmission, again requiring an affirmative selection of the specific recipient prior to transmission.

As one other example, while patient identifiers or patient information is described above as the contextual information used to resolve an intended recipient along with a general recipient descriptor, other embodiments may use other types of contextual information from a patient chart or the like. For instance, a medical facility may have a children's hospital that specializes in treating children under the age of thirteen. Here, when a PCP designates ENT as a recipient descriptor in an e-mail associated with a child, the system may automatically glean the child status from the patient's chart and select an ENT specialist at the facility that works in the children's hospital as the intended recipient for the message.

As still another example, contextual information may be related to the geographic location of a system that receives an electronic message. For instance, where a user composes an electronic message at a first system and specifies "GI 58944" as the recipient, the system may use the recipient indication to identify a GI specialist nearest the zip code 58944 as the intended recipient and may therefore complete the message address with an address targeting the intended recipient.

As another example, an intended recipient need not be a single individual and instead may be a group of individuals associated with a single target or recipient address. For instance, in the above example where a recipient indicator is "GI 58944", the recipient address may be a general address for a GI group closest to the specified zip code, effectively delivering the message to all of the members of the group.

Furthermore, as indicated above, the inventive system may be used in many other industries.

B. Event Based Messaging Systems and Methods and Workflows

The workflows that occur in a modern healthcare system are extremely complex requiring the coordination of many different caregivers that provide specialized services at many associated and un-associated healthcare facilities using many different types of resources to address disparate healthcare needs of diverse populations. Complicating matters is the fact that even affiliated healthcare providers often use different electronic medical record (EMR) software systems and scheduling software systems to manage patient charts and workflows where the different software systems often have different user interface features, layouts and data entry requirements. The different software features and requirements complicate the tasks of data entry and workflow initiation. For instance, to order an MRI procedure, current software systems typically require a physician to specify the MRI procedure using a workflow specifying interface where workflow specifying interfaces may be substantially different at different healthcare entities depending on which software is employed by the entity and where information to be entered to into the interfaces is different depending on the workflow required by the caregiver and where different entities that will handle (i.e., carry out or manage) required workflow require different information to initiate a workflow.

While a modern healthcare system is extremely complex, often times activities performed by specific caregivers within the system are extremely specialized. For instance, radiologists specialize in medical imaging modalities while a neurosurgeon specializes in surgery related to the nervous system. While neurosurgeons routinely require different types of medical images to diagnose solutions to patient problems, in most cases there is no reason for a neurosurgeon to understand all of the steps or sub-processes associated with a workflow to generate a set of diagnostic images. The neurosurgeon simply wants the end image set as quickly as possible. In fact, where several entities in a healthcare system can generate a set of required images, in most cases, a neurosurgeon has no interest in which entity generates the set. All the neurosurgeon is interested in is ordering a desired set of images and obtaining those images quickly and with minimal effort on the part of the neurosurgeon. Any need to use unfamiliar or complex software to initiate a desired workflow increases caregiver frustration with the overall information technology system.

It has been recognized that interfaces exist that substantially all caregivers are already extremely familiar and comfortable with due to widespread use within the communication industry generally. More specifically, most caregivers and people in general routinely use electronic messaging systems such as e-mail to communicate with family, friends and colleagues on a daily basis. In addition, most electronic messaging systems have several common characteristics (e.g., a "To" or target field, a "From" field, a "Subject" field, a message field and an attachments field) so that any caretaker familiar with one electronic messaging system will be immediately familiar with and able to use another electronic messaging system without having to learn new features. Moreover, most healthcare entities already provide e-mail capabilities to all caregivers to enable communication between entity employees.

In the event based messaging system and methods disclosed here, the problems associated with complex and disparate EMR and scheduling software are overcome by enabling caregivers to initiate workflows using familiar and ubiquitous electronic messaging software such as e-mail. To order and initiate a workflow, a caregiver opens an e-mail message template on a computer display screen and, in at least some embodiments, instead of entering an e-mail address for a specific person in the "To" or target field, enters a general descriptor in the target field associated with a workflow the caregiver intends to initiate (i.e., a workflow the caregiver requests). In most cases, when a general descriptor is entered into the target field, a system server identifies contextual information associated with the descriptor and supplements the e-mail message with at least some contextual information that can be used to specify workflow characteristics or to characterize an intended workflow for the purposes of selecting an entity to handle the workflow. For instance, in the case of a physician ordering a workflow associated with a specific patent, a server that automatically supplements a descriptor may be programmed to identify a patient identifier (e.g., a patient ID) in a patient chart and add or at least associate the patient identifier to the e-mail. As another instance, where a caregiver intends to order a period of patient stay in a skilled nurses facility (SNF) after a surgery, when the caregiver enters SNF1 into the target field to request the SNF stay where the "1" indicates specific patient needs (as opposed to SNF2 or SNF3, etc., that indicate other patient needs), a system server may glean the patient's address, age and gender from the patient's chart and add or associate that information automatically to the e-mail being composed by the caregiver. Many other specific examples are contemplated.

In the alternative, the caregiver generating the e-mail message may manually add contextual information to a text message field or some other message field. For instance, a caregiver may manually enter a patient ID number with the general descriptor MRI to manually specify at least some contextual information. When the e-mail message is sent, in at least some embodiments a system server receives the message, identifies a workflow associated with the general descriptor and context information combination and commences the workflow by delivering the message to one or more entities to perform workflow processes. Here, the initiating caregiver need not know which entity is performing the workflow or any of the sub-processes required by the entity to complete the workflow.

Hereinafter, unless indicated otherwise, the term "event" will be used to refer to the ordering of one or more workflows. Thus, for instance, when a physician enters a general descriptor "MRI" into the target field of an e-mail message and sends the message, the sending of the message is considered an event.

In the healthcare industry, while there are several different types of workflows that may be usefully initiated using a system consistent with the present disclosure, three particularly important types of workflows that may be initiated via the system include tests/procedures, referrals/consults and follow-up patient care (e.g., SNF care, physical therapy workflows, psychiatric workflows, etc.).

In the following procedure initiating example, it will be assumed that a neurosurgeon, Dr. White, works at Neurosurgery Institute Inc. (NII), which is affiliated with a large group of medical entities including St. Mary's, LHC, and other medical entities including three different entities that can perform MRI processes within a geographic area. One of the entities that can perform MRI processes is Medical Imaging Inc. (MII). Referring again to FIG. 1, it will also be assumed that server 104 is a messaging server at NII and that related server 102 is NII's EMR system server. In this example, Dr. White is examining a patient, Mr. Tom Ryan, who has been experiencing chronic neck pain for several years. While Dr. White is examining the patient, Dr. White uses pad computing device 113 to access the patient's medical records/chart and to enter information into the patient's chart to memorialize examination results. To this end, see FIG. 5 that shows an exemplary screen shot 500 from pad device 113 where Mr. Ryan's medical chart is presented. The chart screen shot 500 includes, among other things, a patient identifier 502 identifying Mr. Ryan as well as a space 504 in which a subset of patient chart information (not illustrated) is presented. The screen shot also includes a virtual "Create E-mail" icon 506 selectable via touch or cursor movement as well known in the computing industry by Dr. White at any time to generate an e-mail message. During the examination, Dr. White decides to order an MRI process for Mr. Ryan to develop an MRI data set that can be used to generate images to diagnose the cause of the Mr. Ryan's neck pain.

Figure 5:
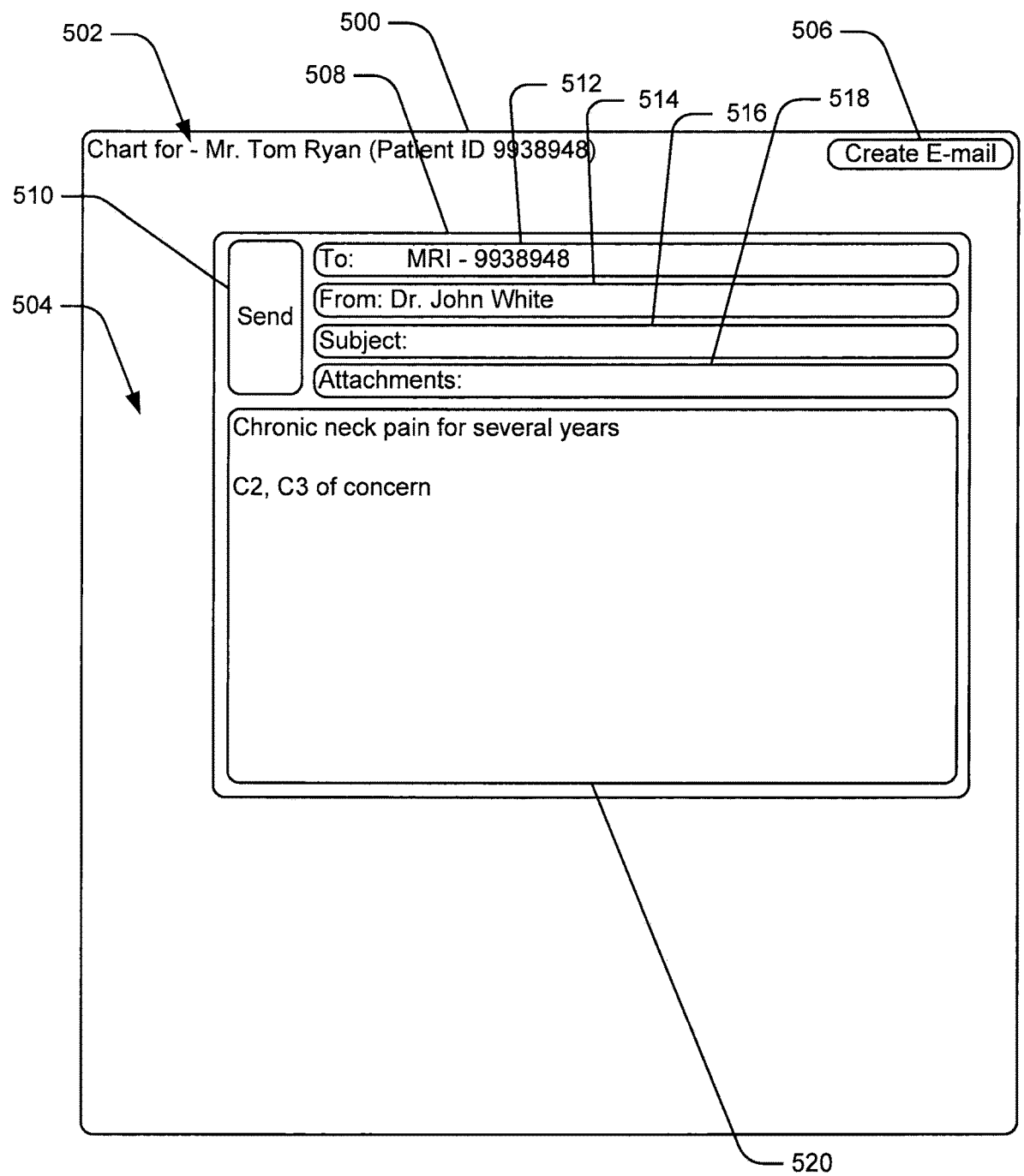
FIG. 5 is a schematic showing an exemplary e-mail message window open over a patient medical chart that shows information in a manner that is consistent with at least some aspects of the present disclosure.

Referring still to FIG. 5, in at least some embodiments, Dr. White uses device 113 to select e-mail icon 506 to open up an electronic messaging (e.g., e-mail) application which, when opened, provides an e-mail message template 508 in a window. Template 508 has a format that is similar to the format of a conventional e-mail message with a virtual "Send" icon 510 for sensing a message after the message is composed, a "To" or target field 512, a "From" field 514, a "Subject" field 516, an "Attachments" field 518 for identifying attachments to the e-mail and a message field 520 for entering message text. Because the message window has a format including fields that are persistently presented in essentially all e-mail applications, most caregivers will be immediately familiar with and comfortable using the format and e-mail application in general. When Dr. White opens an e-mail template 508, e-mail server 104 automatically enters Dr. White into "From" field 514.

Figure 4:
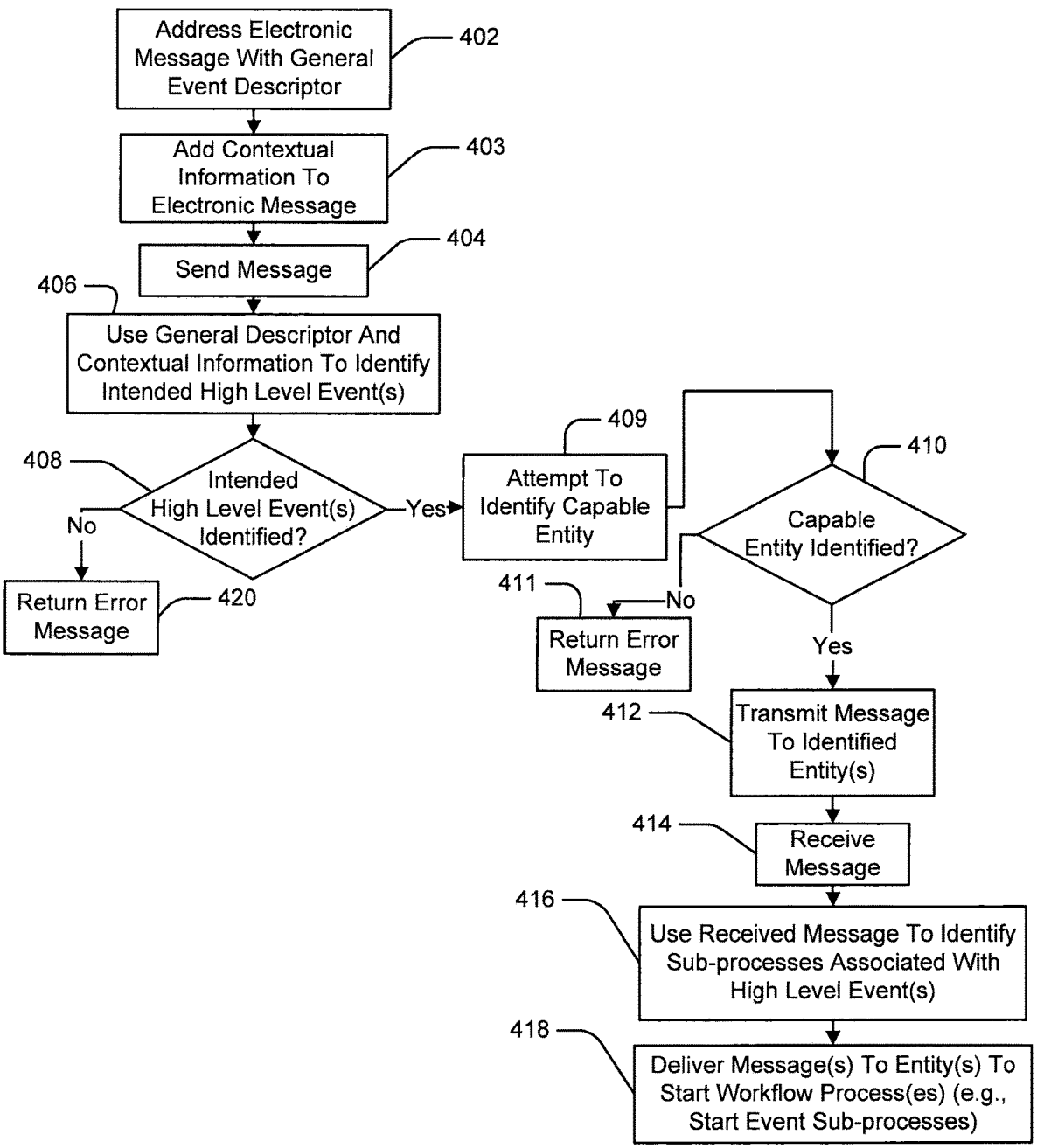
FIG. 4 is a flowchart showing a process for using an e-mail system to initiate a workflow by specifying a general event descriptor.

Referring also to FIG. 4, at block 402, Dr. White uses device 113 to enter a general event descriptor related to an MRI into target field 512. For instance, Dr. White may enter the term "MRI" into field 512. In addition, Dr. White may add other identifiers to target field 512 to send the e-mail to other targets upon transmission. For instance, Dr. White may enter "PCP" as a second target for the e-mail to notify the patient's PCP of the ordered MRI event. As another instance, Dr. White may enter a second general descriptor such as CT in target field 512 to indicate that the doctor intends to initiate a CT scan for the patient. Other e-mail addresses or general event descriptors may also be entered into field 512.

Dr. White may manually enter information into text message field 520 to be transmitted as part of the e-mail message and may also attach other documents or files to the e-mail message including existing images, portions of the patient's medical chart or other types of documentation. For instance, in FIG. 5, the text "Chronic neck pain for several years" has been entered into text field 520. While various types of information may be included as part of, or as attachments to, an e-mail that includes a general event descriptor in the address field, it should be appreciated that such additional information, in at least some embodiments of the disclosure, is not required.

At block 403, contextual information is added to the electronic message. In some embodiments all or a portion of the contextual information may be added manually by Dr. White. For instance, Dr. White may specify a patient identifier for Mr. Ryan which can be used by message server 104 or another system server to determine that the message is associated with Mr. Ryan. In this regard, a more complete descriptor may include "MRI—9938948" where the number 9938948 is Mr. Ryan's patient identification number. Dr. White may manually specify other contextual information such as specific areas of the patient's spine that are of particular concern, other patient symptoms, an initial diagnosis, etc. In FIG. 5, the phrase "C2, C3 of concern" has been entered as contextual information into field 520 to indicate specific areas to be studied. This other contextual information may be added to target field 512 or to some other field such as the message text field 520 as in FIG. 5.

In other embodiments, e-mail server 104 or some other system server may be programmed to monitor target field 512 and, when a general event descriptor is added to the target field, to automatically identify contextual information to be added to the e-mail in the target field, as an attachment, or as a portion of the message text. To support an automated process of adding contextual information to an e-mail, in at least some embodiments, a descriptor-contextual information rules database may be provided and accessible to server 104. To this end, see exemplary database 600 in FIGS. 1 and 6. While database 600 is shown in table format, it should be appreciated that database 600 may take any of several different forms and that the database is shown here in a simplified table format in order to simplify this explanation. Database 600 includes a descriptor column 602, a contextual information column 604 and an e-mail format column 606. Descriptor column 602 lists all general event descriptors supported by the messaging system. For instance, exemplary descriptors include "MRI" which is used to indicate a magnetic resonance imaging procedure, "CT" which indicates a computerized tomography procedure, "SNF1" indicating a specific type of skilled nursing facility activity (e.g., capability to deal with brain trauma), "SNF2" indicating a different type of skilled nursing facility activity (e.g., capability to deal with physical therapy after a spinal surgery), etc. While only a small number of descriptors are shown in FIG. 6, in a working embodiment the system may support several hundred different types of descriptors.

Figure 6:
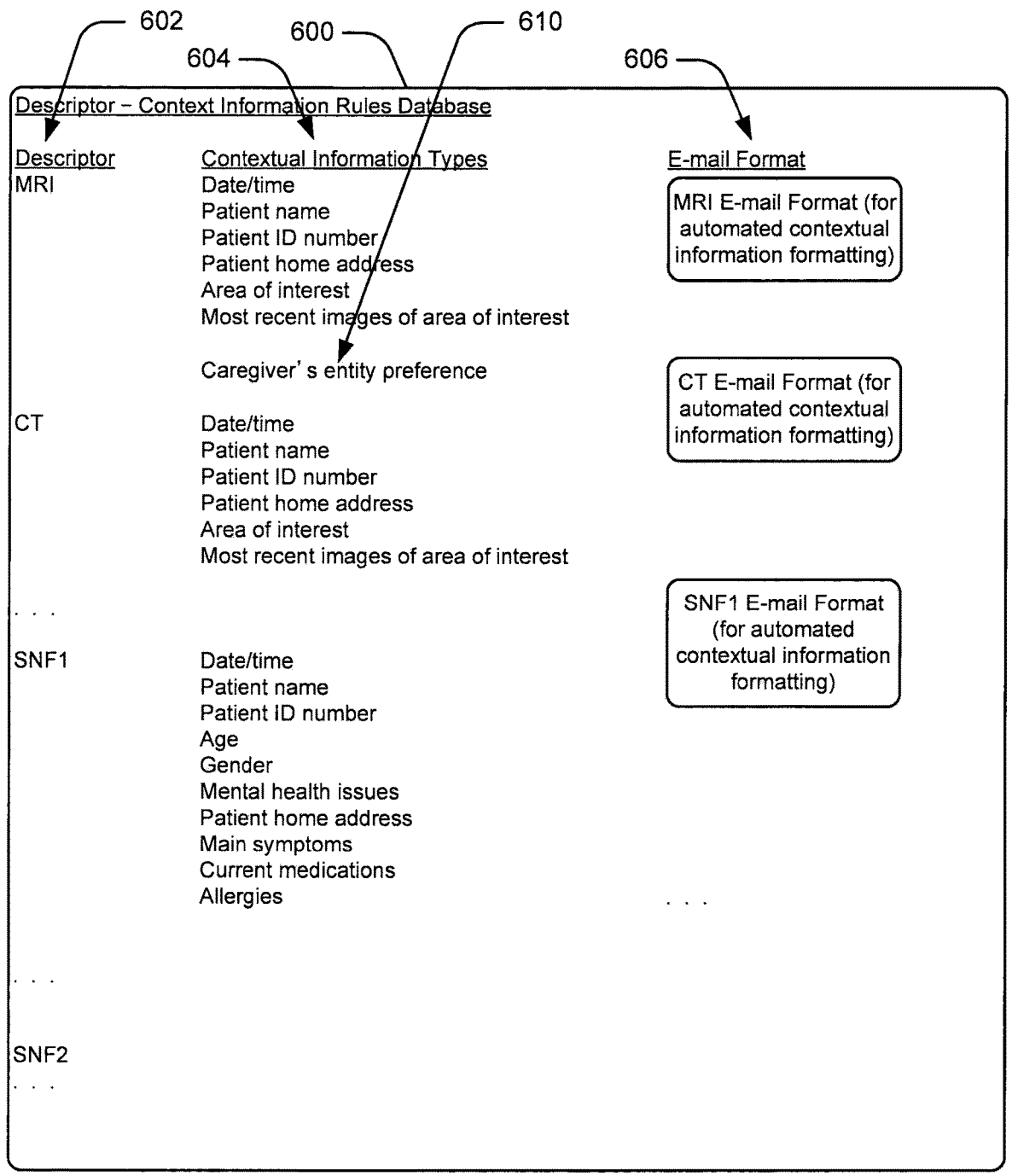
FIG. 6 is a schematic showing an exemplary descriptor-context information rules database.

Referring still to FIG. 6, contextual information column 604 lists contextual information to be obtained and added to or at least associated with general event descriptors in column 602. For instance, column 604 lists date/time, patient name, patient ID number, patient home address, area of body interest and most recent images of area of interest as contextual information that should be obtained when descriptor MRI is specified by a caregiver. Different sets of contextual information may be specified in column 604 for each of the descriptors in column 602 (see that the SNF1 contextual information is a different set than the MRI set). In at least some embodiments all of the contextual information in column 604 may be gleaned from a patient's medical chart. In this regard, medical records already have specified fields that can be accessed to obtain contextual information. In other embodiments, at least some of the contextual information may be gleaned from other sources such as, for instance, an electronic caregiver file. For example, a specific caregiver may have a specific preference for one entity over others for certain types of workflow. In FIG. 6, a caregiver's entity preference is provided in contextual information column 604 for the descriptor MRI.

Thus, in the present example, server 104 may glean all of the contextual information specified in column 604 for descriptor MRI from the patient's chart most recently accessed or currently accessed by Dr. White or from other sources to be automatically added to the message. For instance, in FIG. 5, after Dr. White enters "MRI" into field 512, server 104 may automatically glean Mr. Ryan's patient ID number and the text shown in field 520 from Mr. Ryan's chart information 504 and add that information to the message being composed using template 508.

Some of the contextual information in column 604 may be optional. For instance, while a caregiver may specify a caregiver's entity preference 610, some caregivers may have no preference and therefore may simply allow the system to select a suitable caregiver to handle requested workflows. Where the entity preference is optional, server 104 would be programmed to check if there is a caregiver preference associated with a descriptor and use the preference if it exists or simply select a suitable caregiver if the preference has not been specified in the caregiver's file.

Some of the contextual information may be required. For instance, patient identifying information is almost always required. If a caregiver attempts to generate an event based message and server 104 is unable to automatically obtain patient identifying information, the server 104 may be programmed to request the patient identifying information from the caregiver by opening a warning window indicating required information and presenting a field for the caregiver to enter the patient identifying information. For instance, if a caregiver opens a blank e-mail message in a way that the message is not correlated with a specific patient's chart and enters an "MRI" descriptor in the target field, server may have no way to automatically identify the patient associated with the workflow being requested. In this case, a warning and requirement for identifying information would be generated.

Referring again to FIG. 6, database 600 also includes an e-mail format column 606. Column 606 includes separate format specifying information for each of the descriptors in column 602 indicating how contextual information in column 604 should be arranged in the e-mail being generated by a caregiver. For instance, in the case of the MRI descriptor in column 602, there is an MRI e-mail format in column 606 that may specify the simple format shown in FIG. 5 for adding the patient name and ID number to target field 512 as well as the "C2 and C3 of concern" text to field 520. Much more complex format information is contemplated and several examples are provided hereafter.

In other embodiments, instead of adding all contextual information that may be required to initiate one or more workflows to one or more fields in the electronic message, messaging server 104 may simply add a contextual information access key to the message being composed to enable system servers to subsequently access contextual information associated with the general event descriptor. For instance, a patient identifier (e.g., an eight digit patient specific ID number) may serve as a contextual information access key. In this case, a complete electronic message may simply include the general event descriptor (e.g., "MRI") and the patient identifier (see information in field 512 in FIG. 5) as a contextual information access key, and no other information would be required in the electronic message to initiate one or more workflows.

While systems may support many different general event descriptors (e.g., hundreds in some cases), it is contemplated that most caregivers will only routinely use a small subset (e.g., 15) of the descriptors and therefore caregivers will quickly learn descriptors that they use consistently. In some cases, however, it is recognized that a caregiver will have the need to request a workflow associated with an unknown general event descriptor. To help caregivers identify general descriptors that are only seldom used, in at least some embodiments, when a caregiver begins to enter a general descriptor into field 512, server 104 may be programmed to examine the entered descriptor, identify supported descriptors that are similar to the entered descriptor and provide a list of possible descriptors intended by the caregiver. The list may be presented as a drop down menu including selectable descriptors. The list may also include descriptions of the workflows associated with each general descriptor to help the caregiver identify an intended descriptor.

In the present example, unless indicated otherwise, it will be assumed that server 104 identifies the MRI descriptor in the target field and is programmed to, in response, automatically identify the contextual information in column 604 of database 600 that is associated with the MRI descriptor in column 602 including Mr. Ryan's name and patient ID number as well as "Chronic neck pain for several years" and "C2 and C3 of concern" notes from Mr. Ryan's chart and add that contextual information to fields 512 and 520 as shown in FIG. 5 and as specified by the MRI e-mail format in column 606.

Referring still to FIGS. 1, 4 and 5, at block 404, Dr. White selects send icon 510 to transmit the message including the general event descriptor and the contextual information added to the message to e-mail server 104. At block 406, upon receiving the message, server 104 uses the general descriptor to identify one or more high level events or workflows that Dr. White intends to initiate for Mr. Ryan. For instance, the high level event in the present example is an MRI procedure for Mr. Ryan. In some cases, at block 406, server 104 may use the contextual information in addition to the general descriptor to identify one or more workflows intended by Dr. White. For instance, in the present example, server 104 may use the chronic neck pain information in the message as well as the C2 and C3 information to identify a head and neck MRI workflow as an intended high level event requested by Dr. White.

In the alternative, in a case where the e-mail only includes the general event descriptor "MRI" and the patient ID number as a contextual information access key, upon receiving the e-mail, in some embodiments, server 104 is programmed to use the access key to gain access to the patient's chart stored by server 102, identify contextual information in the chart relevant to identifying a requested high level event and to use that contextual information and the general event descriptor to identify a requested workflow. In the present example, server 104 identifies a head and neck MRI workflow using the descriptor and contextual information.

At block 408, if server 104 cannot identify at least one intended high level event using the descriptor and the context information, control passes to block 420 where server 104 generates and transmits an error message to Dr. White indicating that no intended event has been identified. This and other error messages in this disclosure may take any of several different forms including an e-mail, a text message, a voicemail message, etc.

At block 408, when an intended event is identified, control passes to block 409 where server 104 attempts to identify at least one entity capable of handling the identified intended event. At block 410, if server 104 cannot identify an entity capable of handling an intended event, control passes to block 411 where an error message is generated and transmitted back to Dr. White indicating that no capable entity was identified. For instance, if the identified intended event is a specific type of MRI procedure that none of the entities associated with the system is capable of performing, an error message indicating no capable entity would be transmitted to Dr. White.

At block 410, once a capable entity is identified, control passes to block 412 where an e-mail message is transmitted to the identified entity to initiate the workflow requested by Dr. White. Here, the transmitted message may be supplemented with additional information by server 104 such as, for instance, a specific type of MRI procedure associated with the contextual information in the original message. In the alternative, the original message sent at block 404 may be transmitted to the capable entity.

Referring still to FIGS. 1 and 4, when the message is received by a capable entity at block 414, the capable entity handles the requested workflow. Handling a workflow may include performing all sub-processes that comprise the workflow. In the alternative, handling a workflow may include managing other entities that perform workflow sub-processes or performing a subset of the sub-processes and managing another subset of the sub-processes as they are performed by other entities. For instance, in the present MRI example, assume that the message receiving entity is Medical Imaging Inc. (MII). To perform an MRI of a patient's head and neck, MII may require several sub-processes including an MRI scheduling procedure, a pre-MRI consult two days prior to the actual MRI procedure, an MRI setup procedure, the actual MRI data generating procedure and a data set review procedure for assessing the quality of generated MRI data set prior to transmission back to the ordering physician. MII may sub-contract to a scheduling entity to perform the scheduling process and to a consult entity to prepare patients for imaging procedures two days prior to the scheduled times of the procedures. In this case, handling the MRI workflow includes identifying sub-processes, identifying entities capable of completing the sub-processes and transmitting messages to the capable entities to initiate the sub-processes. The messages to the additional capable entities may comprise instances of the original e-mail message generated by Dr. White or may include a more detailed message requesting one or more sub-processes to be performed along with contextual information.

In the above example, while Dr. White would like to obtain an MRI data set for studying physiological characteristics of Mr. Ryan's head and neck, there is no reason for Dr. White to understand all of the sub-processes required to generate the data set. In addition, in many cases, there is no reason for Dr. White to even know which entities within a set of affiliated entities will perform the sub-processes associated with the MRI study. Moreover, where Dr. White works at NII, there is no reason for NII to understand all of the sub-processes required at MII or other affiliated entities to perform MRI procedures. Instead, a system consistent with the present disclosure only calls for Dr. White to provide a short general event descriptor related to a requested workflow which a system server can automatically supplement with basic contextual information where the general descriptor and basic contextual information can then be used by MII or some other imaging entity to complete the requested workflow and return the desired MRI data set.

Figure 7:
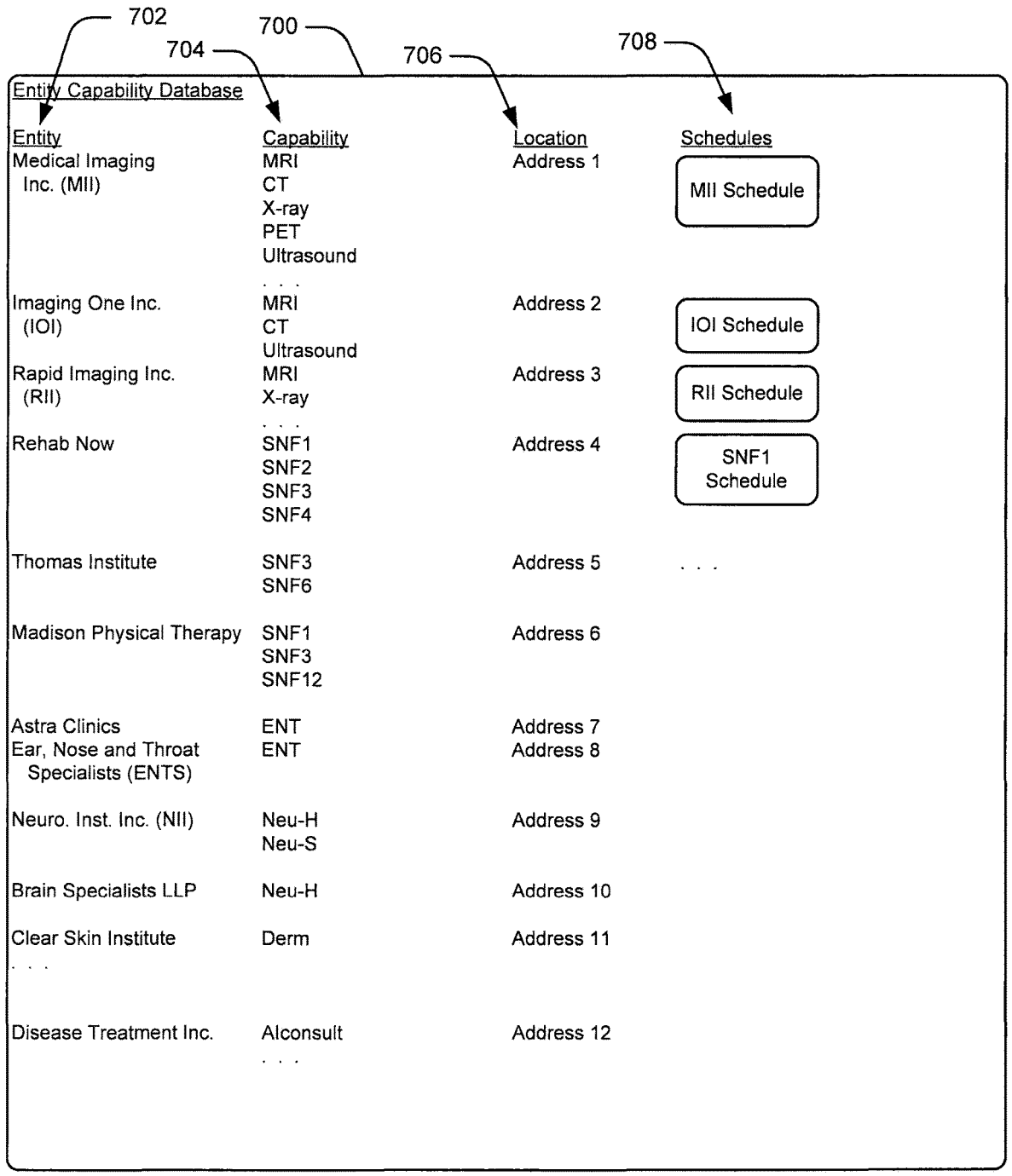
FIG. 7 is a schematic showing an entity capabilities database.

Referring again to FIGS. 1 and 4, server 104 may perform step 409 to attempt to identify a capable entity by accessing a database that stores entity capability information that associates healthcare entities with the general descriptors or with the general descriptors and contextual information supported by server 104. For instance, referring to FIGS. 1 and 7, an exemplary entity capability database 700 that may be accessible by server 104 is illustrated. While shown in table form in order to simplify this explanation, the entity capability database may take any of several different forms useful to associate entities with specific capabilities. In addition, while simple entity and capability information is shown in exemplary database 700, more complex information is contemplated and would likely be supported by the overall system.

Table 700 includes an entity column 702 and a capabilities column 704. Entity column 702 lists all medical entities capable of performing specific requested workflows. To this end, column 702 includes Medical Imaging Inc. (MII) and Neurosurgery Institute Inc. (NII) referenced in the above example as well as other entities including radiology entities Imaging One Incorporated (IOI) and Rapid Imaging Inc. (RII), skilled nursing facilities Thomas Institute and Madison Physical Therapy, ENT specialists Astra Clinics and ENTS, another entity capable of handling neurosurgery workflows Brain Specialists LLP, a dermatologist Clear Skin Institute, an entity specializing in auto immune diseases Disease Treatment Inc., and others. Column 704 lists general event descriptors associated with capabilities for each of the entities in column 702. For instance, column 704 indicates that MII is capable of performing imaging procedures using various imaging modalities including MRI, CT, X-ray, PET and ultrasound, that Rapid Imaging Inc. is capable of only MRI and X-ray, Rehab Now is capable of providing skilled nursing follow-up care for patients having characteristics requiring any one of SNF1, SNF2, SNF3 or SNF4 capabilities, Madison Physical Therapy is capable of providing skilled nursing follow-up care for patients having characteristics requiring any one of SNF1, SNF3 or SNF12 capabilities, NNI is capable of performing both head (Neu-H) and spine (Neu-S) neurosurgery consultations, etc.

Thus, in the illustrated example, at step 409 e-mail server 104 accesses database 700 and identifies all entities capable of performing or managing the workflow associated with the general descriptor in the received e-mail. For instance, in the present example where Dr. White specified an MRI, server 104 identifies each of MII, IOI and RII as capable entities.

Where more than one entity is capable of performing or managing a workflow, any of several different sub-processes may be used to select one of the capable entities for a specific workflow. For example, in some cases server 104 may simply send the workflow message to a first entity within database 700 that is capable of handling a workflow. As another example, server 104 may use other contextual information to attempt to optimize entity use based on either expressed or probable patient preferences, caregiver preferences, entity preferences (e.g., NII may have a policy of always using MII for imaging unless a different preference is expressed) or other system preferences. As still one other example, server 104 may be programmed to identify a geographically optimal capable entity based on the location of a requesting physician and capable entities, a patient's home or business address and locations of capable entities, etc. In this regard see column 706 in FIG. 7 where database 700 includes addresses of entities that may handle workflows.

As one other example, server 104 may have access to entity scheduling information and may be able to identify relative availability of capable entities to handle requested workflow(s). For instance, in some cases, other entities may provide scheduling information to server 104 that indicates availability to handle various workflows. Referring again to FIG. 7, server 104 may store the scheduling data in a Schedules column 708 for each of the entities in column 702 in database 700. When an e-mail including a general event descriptor is received, the step of identifying a capable entity may include using the scheduling information to determine availability of an entity to handle the workflow associated with the general event descriptor within some required time period after the request is generated.

When any artificial intelligence (AI) system gleans contextual information from a database and uses that information to identify a process or workflow to perform, there is always the possibility that the system will make a mistake and may identify an unintended workflow. In the case of a healthcare system, the consequences of identifying an unintended workflow can be wasteful at best (e.g., a duplicative test) and can result in very bad consequences of several types for patients (e.g. unneeded procedures, unnecessary medications, etc.). For this reason, in at least some embodiments of the present disclosure, prior to initiating any workflow identified using automatically gleaned information, some notice of the identified workflow is presented to a requesting caregiver to at least make the caregiver aware that a workflow has been requested.

Figure 8:
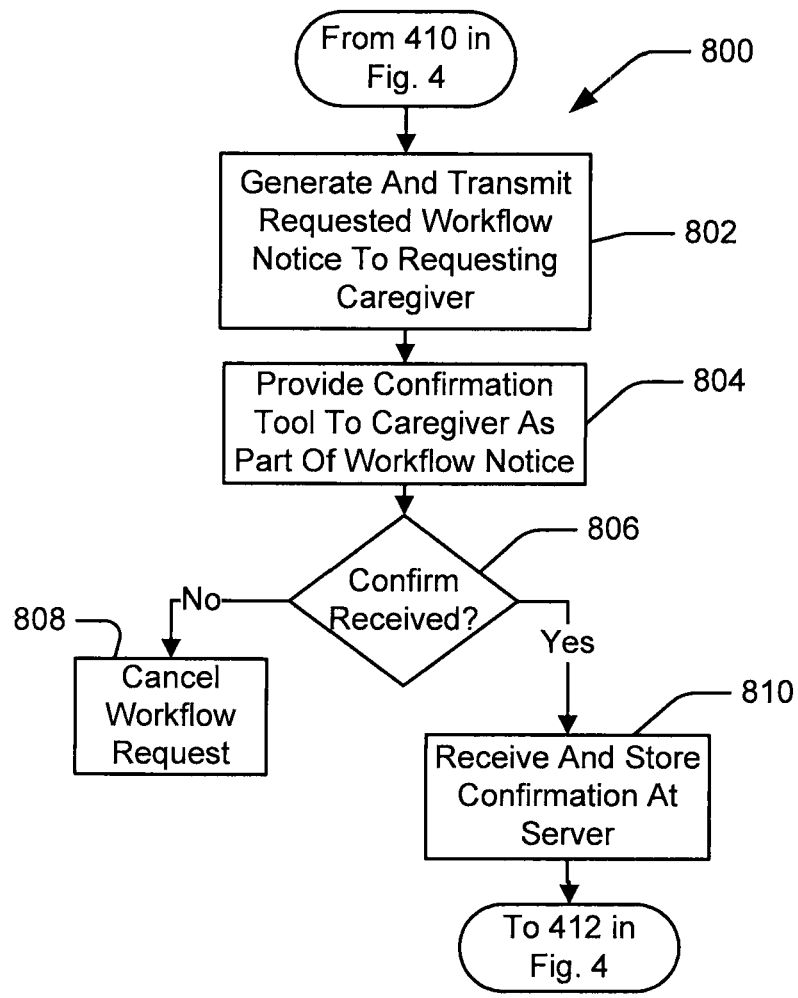
FIG. 8 is a flowchart showing a sub-process that may be included as part of the FIG. 4 process for facilitating a warning and confirmation process for a requested workflow.
Figure 9:
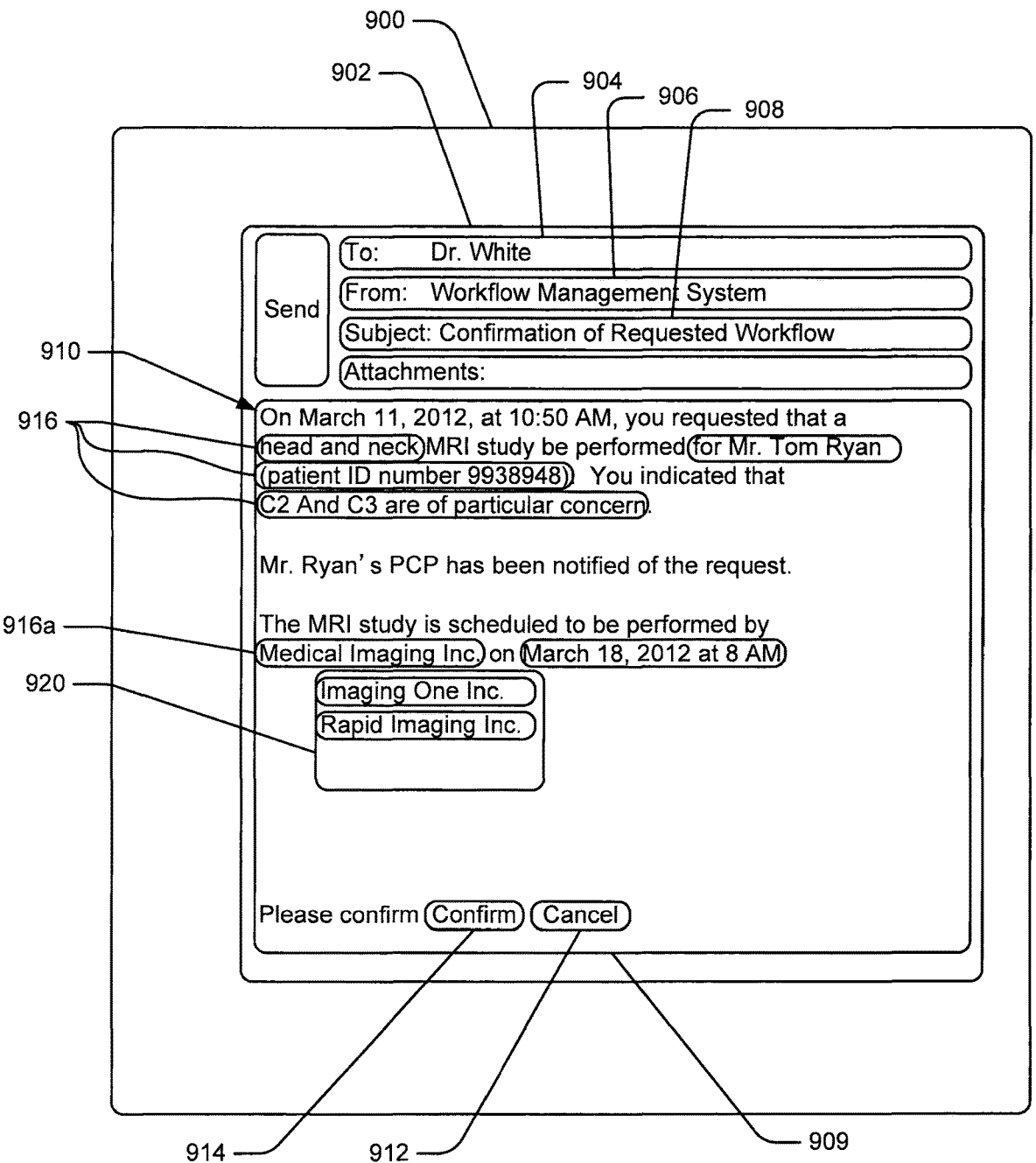
FIG. 9 is a schematic similar to FIG. 5, albeit showing a confirmation notice message.

In the above example, referring again to FIGS. 1 and 4, after server 104 uses the general descriptor and contextual information to identify a head and neck MRI workflow at block 408 and identifies MII as the entity to handle the workflow at block 410, control may pass to block 802 in sub-process 800 shown in FIG. 8 where an e-mail or other electronic messaging system is used to generate and transmit a notice to Dr. White. The notice may specifying that Dr. White requested a head and neck MRI workflow for Mr. Ryan which will be conducted by MII as well as other relevant information (e.g., the date and time the request was made, a "required by" date, etc.). For instance, see the exemplary e-mail notice 902 that may be presented via a screen shot 900 on device 113 in FIG. 9. Exemplary e-mail notice 902 has the general appearance of a typical e-mail including a target field 904 specifying Dr. White, a from field 906 specifying that the e-mail was generated by the workflow management system, a subject field 908 identifying that the e-mail is a workflow confirmation notice and text 910 in a message field 909 describing the workflow requested. Referring again to FIG. 6, the format of the notice e-mail 902 may be specified in column 606 of database 600.

In at least some embodiments it is contemplated that any contextual information automatically added by a system server to the workflow request is highlighted in a request notice sent to a requesting caregiver so that the caregiver receiving the notice can quickly identify information the system automatically added and distinguish that information from any contextual information that was manually added by the caregiver. For instance, in FIG. 9, numeral 916 earmarks contextual information in field 909 that was automatically added by server 104 to distinguish that information from other information. This feature enables a caregiver to quickly focus on automatically added supplemental contextual information to confirm that the added information is consistent with the caregiver's intent.

In embodiments where server 104 provides a simple notice of requested workflow to a requesting caregiver, after block 802 in FIG. 8, control may pass back to block 412 in FIG. 4 where a message is transmitted to a capable entity to initiate the requested workflow.

In other embodiments, the requested workflow message may include a confirmation tool inviting the requesting caregiver to manually confirm the workflow request prior to initiation. To this end, see block 804 where a confirmation tool is presented as part of the notice e-mail to the requesting caregiver. See also FIG. 9 where virtual "Confirm" and "Cancel" icons 914 and 912, respectively, are included in the e-mail text field 909 that are selectable to confirm or cancel the workflow specified in the notice e-mail 902. At block 806, if the caregiver rejects the workflow specified in the notice by selecting the cancel icon, the process stops at block 808. If the caregiver confirms the workflow specified in the notice by selecting the confirm icon, the confirmation is received by server 104 at 810 and is stored after which the process continues back to block 412 where the workflow is initiated.

In at least some embodiments a requested workflow notice e-mail may also include tools for modifying the workflow specified by the notice e-mail. For instance, where information that was automatically added by server 104 to the general descriptor is highlighted, the e-mail may enable a caregiver to select a highlighted portion of the text to access other options. For example, in FIG. 9, if Dr. White touches or otherwise selects a highlight 916*a* that distinguishes entity identifier "Medical Imagining Inc., a drop down menu 920 opens up with other entities capable of performing the requested workflow. In the example, entities "Imaging One Inc.," and "Rapid Imaging Inc." are represented in menu 920. By selecting one of the entities in the drop down menu, Dr. White can swap the selected entity for MII in the text message and workflow generally.

Changes to any of the information in the fully specified e-mail may ripple through other e-mail information. For instance, in FIG. 9, where Imaging One Inc. is swapped for MII in the text message, the change may result in an update of the date and time of the MRI procedure to reflect a time open in a schedule for Imaging One, etc. Other rippling changes are contemplated.

The workflow process may be specified in the notice e-mail in a simplified manner or in great detail. In this regard, in many cases the notice e-mail can be provided to a requesting caregiver almost immediately after the caregiver sends the original e-mail to server 104. For this reason, the caregiver should have a clear memory of the request and the caregiver's intention and therefore limited information should usually suffice in the confirmation notice. For instance, a confirmation notice may simply specify a desired work product for a specific workflow. In the present example, the notice may simply specify "You requested a head and neck MRI for Mr. Ryan".

Another way to provide notice of a workflow being requested by a caregiver is to provide notice prior to a caregiver actually sending or submitting an event based e-mail or other electronic message to the system. In this regard, in at least some embodiments, server 104 may monitor the target field in an e-mail and, when a general event descriptor is recognized in the field, may identify contextual information related to the general event descriptor (e.g., glean related information from a patient chart), use the descriptor and related contextual information to identify a likely intended workflow, identify an entity capable and available to handle the workflow and use the identified information to populate fields of the e-mail to fully specify a likely intended workflow essentially in real time (e.g., all within 2-3 seconds). The caregiver can review the fully specified e-mail and select the send icon to initiate the workflow specified by the e-mail.

Figure 10:
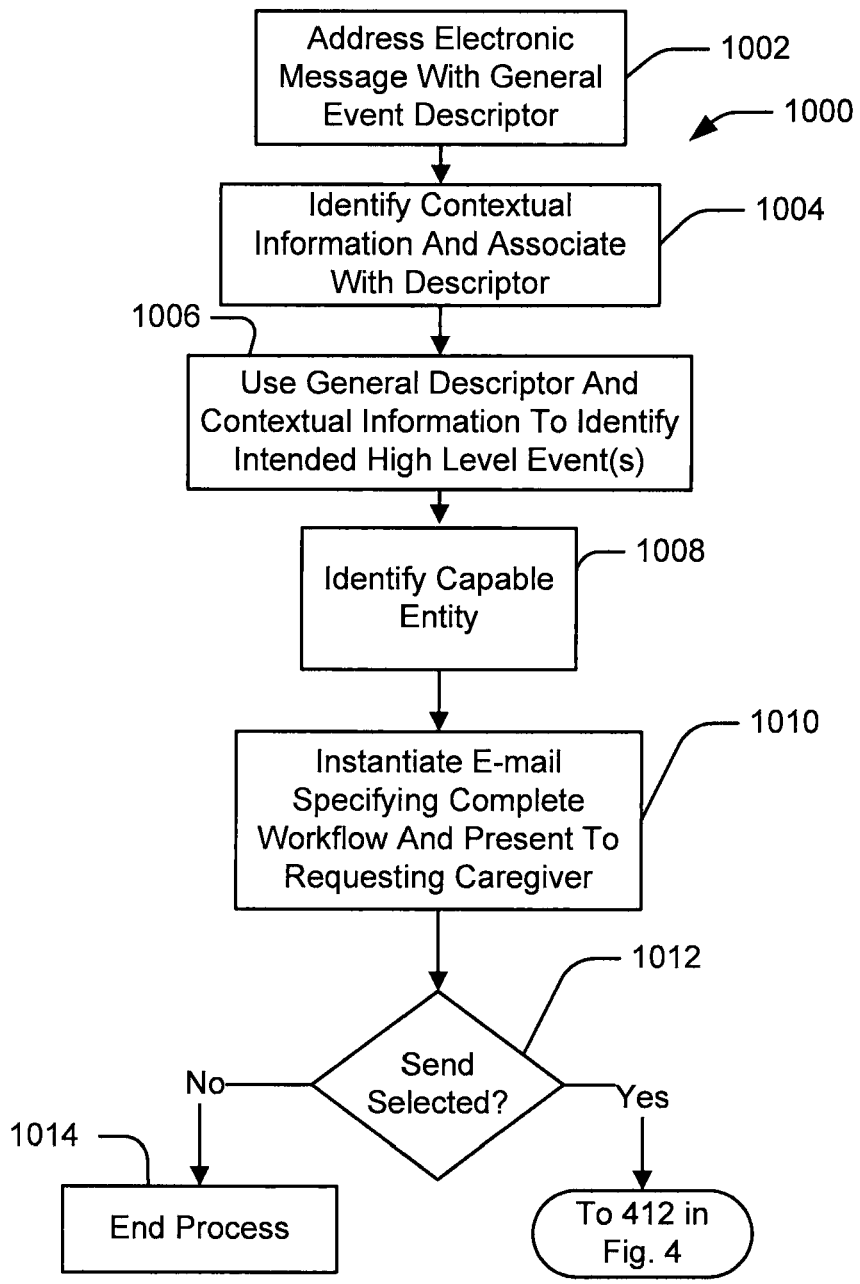
FIG. 10 is a flowchart showing a process for automatically adding workflow specifying information to an e-mail after a simple event descriptor has been entered by a caregiver.
Figure 11:
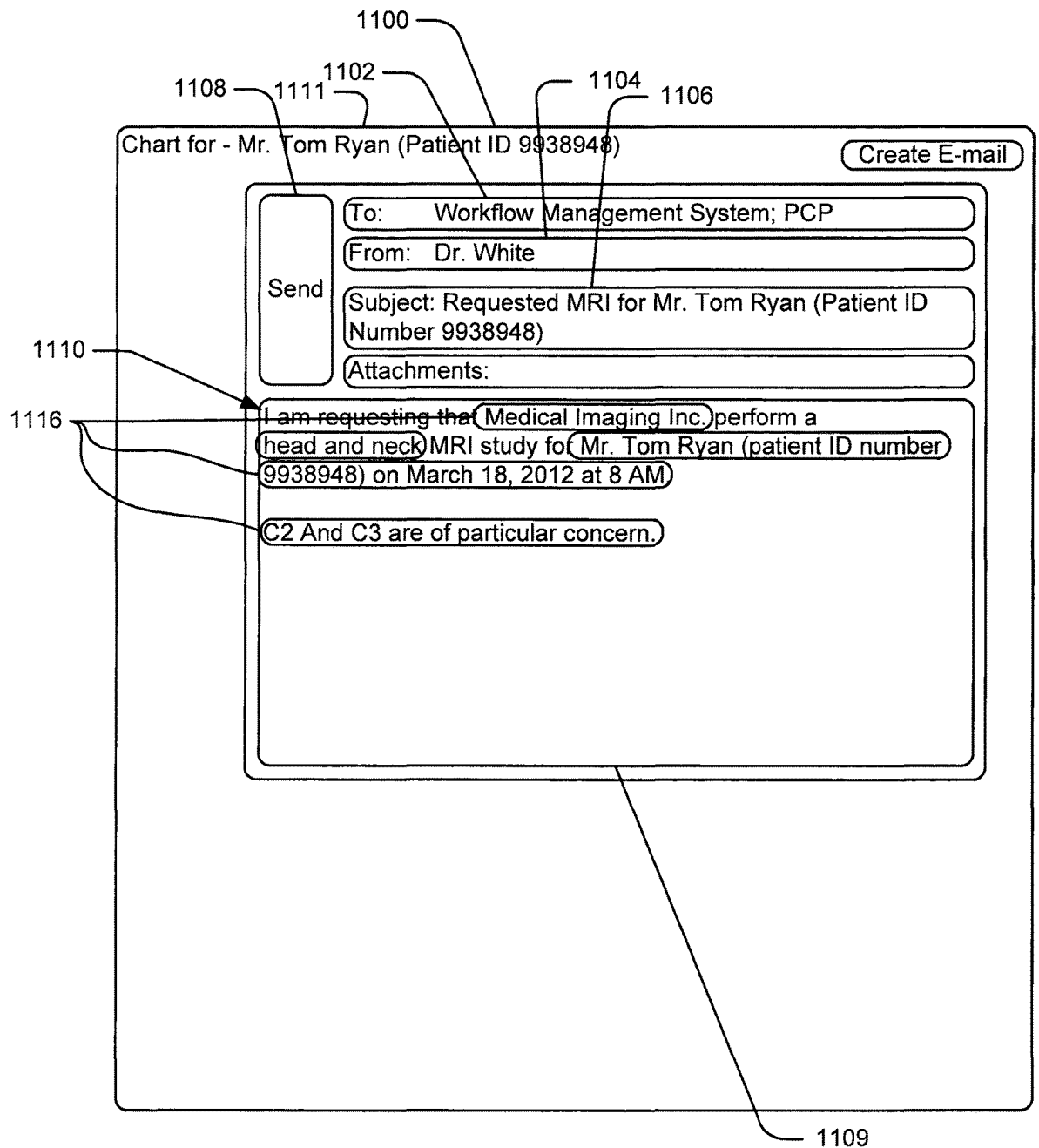
FIG. 11 is an exemplary e-mail that may result from the process of FIG. 10.

A process 1000 for using a general event descriptor and related contextual information to generate a fully specified workflow e-mail is shown in FIG. 10. Continuing with the MRI example above, referring also and again to FIG. 1 and also to FIG. 11 where an exemplary e-mail message/window 1101 is shown over a screen shot 1100 of Mr. Ryan's medical chart, at block 1002, Dr. White uses device 113 to enter the term "MRI" into field 1002. In FIG. 11, the e-mail is shown in a later fully specified state where server 104 has automatically replaced the initial "MRI" descriptor with the phrase "Workflow Management System; PCP" as will be described hereafter. In this embodiment, server 104 monitors field 1102 and identifies the "MRI" descriptor immediately upon entry and prior to Dr. White selecting send icon 1108.

At block 1004, server 104 uses the general descriptor (e.g., "MRI" in the present example) to identify relevant contextual information from Mr. Ryan's chart that is currently open or from any other source (e.g., Dr. White's preferences, NII's preferences, etc.). At block 1006, server 104 uses the general descriptor and contextual information to identify one or more high level events or workflows likely intended by Dr. White. At block 1008, server 104 identifies at least one entity capable of performing the high level event or each of several identified high level events. In the present example, consistent with the description above, server 104 may identify a head and neck MRI to be completed within one week and MII as a capable entity as well as Dr. White's note that C2 and C3 are of concern.

Referring still to FIGS. 1, 10 and 11, at block 1010, server 104 automatically populates various fields in e-mail message 1101 with workflow specifying information prior to Dr. White selecting send icon 1108. For instance, the phrase "Requested MRI for Mr. Tom Ryan (Patient ID Number 9938948)" is automatically entered into subject field 1106 clearly indicating an intended workflow. Text further describing the workflow is generated and added to text field 1109. In the example, text in field 1109 further specifies that the study should be a head and neck MRI study, that MII should perform the study, the time and date on which the study will be scheduled to occur and that C2 and C3 are of particular concern. Referring again to FIG. 6, format information for formatting e-mail message 1102 for an MRI request may be stored in column 606 of database 600.

Another automatic modification to the e-mail includes swapping one or more e-mail addresses for the general event descriptor in target field 1102. For instance, in the example illustrated in FIG. 11, after Dr. White enters "MRI" into field 1102, server 104 automatically swaps two targets for the "MRI" descriptor including the "Workflow Management System" and "PCP", meaning Mr. Ryan's PCP.

Referring again to FIGS. 1, 10 and 11, at block 1012, once Dr. White selects send icon 1108, control passes back to block 412 in FIG. 4 where the message is transmitted to the entity that will initiate the requested workflow. If Dr. White fails to select the send icon, the e-mail is never sent and the workflow is cancelled at block 1014.

While the system above is described as one where e-mail server 104 performs the process of identifying high level requested events and workflows and entities to handle workflows, it should be appreciated that all or a subset of those processes may be performed by any other system server or set of servers or using server 104 and one or more other servers to perform different subsets of the disclosed process. For instance, in FIG. 1, server 104 may route received e-mails including general descriptors and some contextual information to server 102 and server 102 may access databases 600 and 700 and run applications for identifying intended workflows and entities to handle the workflows. In other cases, server 104 may route e-mails including general descriptors on to other system e-mail servers (e.g., 106 in FIG. 1) and the receiving servers may each assess their own capability and availability to handle (e.g., perform or manage) requested workflow(s) with one of the servers accepting the workflow and notifying server 104 and/or all of the other servers that the accepting server will handle the workflow(s). This process is sort of a workflow auction or shopping process whereby any server associated with an entity that may be at least somewhat optimal for handling a workflow can accept workflow responsibilities.

While some aspects of various embodiments of the present disclosure are described above, it should be appreciated that many other aspects and variations are contemplated. For instance, while the embodiments described above call for an electronic message that closely resembles a typical e-mail format, in other embodiments it is contemplated that an electronic message may have one or more additional fields specifically earmarked for entering an event based message to initiate a workflow. For instance, an additional "Workflow" field may be included when an e-mail message is opened for entering a general event descriptor. The additional workflow field may reduce caregiver confusion with how the e-mail system works to initiate workflows via entry of a descriptor into a target field. In other embodiments, instead of entering a general descriptor in the target field, the system may support entry of the general event descriptor in other fields (e.g., the "attachments" field).

In other embodiments, when a general descriptor is entered into the target field to initiate a workflow, the descriptor may need to be followed by ".org" or some other designator (e.g., ".ged" to indicate "general event descriptor") which can be recognized as indicating that the term or phrase just prior to the designator should be treated as a general event descriptor. For instance, "MRI" in this case would only be recognized as a general event descriptor when followed by .org, the term "consult" would only be recognized as a general event descriptor when followed by .org., and so on.

While contextual information is shown and described above as being added directly to the content of an e-mail message in visible message fields such as the target field, the message text field, or other fields, in other embodiments the contextual information may not be added to the visible fields and instead may simply be associated with the e-mail and transmitted therewith.

While the examples described above are in the context of the medical and healthcare industries, various embodiments of the disclosure will be useful in other industries. For instance, an event based e-mail system will be useful in the construction industry where project files exist and a system user may want to kick off a workflow associated with a specific project. In this case, for instance, a system user reviewing final plans for a project on a computer may open an e-mail message and enter the descriptor "Order materials" in a target field. Here, the a system consistent with at least some aspects of the present disclosure may, in response to the descriptor, glean all materials requirements from the project file, identify an entity capable of delivering all of the required materials at different scheduled times and at a desired cost and may initiate one or more workflows when the user selects the send icon.

As another instance, an event based e-mail system will be useful in manufacturing industries where orders may be specified prior to actual manufacturing of products for customers. Where an order is electronically stored and is being reviewed by a system user, the user may open an e-mail and enter the descriptor "Place order" thereby causing the system to start one or more workflows associated with the ordering process.

In at least some embodiments caregivers or other system users may be able to customize their e-mail systems to support customized event descriptors, store caregiver preferences for workflow handling entities, contextual information to glean from different sources, turn around time requirements for different workflows, how notice of requested workflows will be received for confirmation purposes, etc.

Accordingly, the scope of the invention should be determined from the following claims and not limited by the above disclosure.

I claim:

1. A computer system for initiating at least one workflow associated with a patient through electronic messaging, the system comprising:
an electronic medical records server in communication with a patient chart database including patient medical records for an associated patient, the patient records comprising specified fields containing contextual information related to the patient;
an e-mail server in communication with the electronic medical records server and a user interface including a display and at least one user input device, the e-mail server in communication with an electronic message template comprising a plurality of fields including a target field for receiving a general event descriptor and a message text field for providing a message related to a workflow corresponding to the general event descriptor, the e-mail server further in communication with:
a rules database correlating an electronic message format for the message text field with the general event descriptor and contextual information related to the medical workflow;
an entity capability database identifying entities and capabilities related to the medical workflow;
the e-mail server comprising a processor programmed to:
present the electronic message template on the display of the user interface;
receive the general event descriptor in the target field;
receive a patient identifier in the target field;
access the rules database using the general event descriptor to identify the medical workflow corresponding to the general event descriptor, to identify an electronic message format corresponding to the general event descriptor and the identified patient, and to format the message text field consistent with the general event descriptor;
access the patient chart database using the general event descriptor to populate the fields in the electronic message with contextual information corresponding to the general event descriptor and the patient identifier, wherein the patient identifier is used as an access key to the patient chart database and the specified fields in the patient chart database identify the contextual data;

access the entity capability database using the general event descriptor to identify at least one entity capable of performing the medical workflow corresponding to the general event descriptor; and transmit the electronic message to the identified at least one entity to initiate the workflow.

2. The computer system of claim 1, wherein the processor is further programmed to provide a confirmation tool configured to receive input from the user input device to initiate the workflow.

3. The method of claim 1, wherein the electronic message template further comprises an attachment field configured to receive attached documents.

4. The method of claim 1, wherein the electronic message template further comprises a field for identifying the requester of the workflow.

5. A computer-implemented electronic messaging method for initiating at least one medical workflow for a patient, the method comprising the steps of:

providing a processor programmed to perform the steps of:

presenting an electronic message template via a display wherein the electronic message includes at least one target field configured to receive a general event descriptor and at least one message field adapted to provide contextual information related to the general event descriptor;

associating the electronic message template with a patient identifier;

receiving the general event descriptor via an interface in the target message field and using the general event descriptor to access a rules database to identify at least one medical workflow;

using the general event descriptor to format a message in the message field to provide contextual information for a workflow corresponding to the general event descriptor, using the patient identifier to access corresponding contextual information in pre-defined fields in a corresponding patient chart, and providing the corresponding contextual information in the message field;

using the general event descriptor to access an entity capability rules database to identify at least one entity that is capable of providing the workflow identified by the general event descriptor in the target field; and transmitting an electronic message including the message field to that at least one entity that is identified to be capable of providing the workflow being requested by the user to initiate the workflow being requested.

6. The method of claim 5 further including the step of using the contextual information to identify the workflow.

7. The method of claim 6 wherein patient charts including patient medical records are stored in a database, and the step of accessing contextual information includes accessing information in the database.

8. The method of claim 6 further including the steps of providing a rule set that correlates general event descriptors with contextual information types, the step of accessing contextual information includes using the rule set to identify contextual information types correlated with the general event descriptor and identifying information corresponding to the identified contextual information type in the patient chart as patient contextual information.

9. The method of claim 6 wherein the step of associating patient contextual information with the electronic message includes adding a patient identifier to the electronic message.

10. The method of claim 5, wherein the electronic message template further comprises an attachment field configured to receive attached documents.

11. A computer-implemented electronic messaging system for initiating at least one workflow associated with a patient, the method comprising the steps of:

a database including patient charts, each patient chart including patient medical records for an associated patient, the patient medical records including pre-defined fields;

a rules database;

an entity capability database; and a processor, the processor programmed to:

present an electronic message template via a display wherein the electronic message includes fields including a target field and a message field;

receiving a general event descriptor and a patient identifier in the target field via an interface and utilizing the general event descriptor to format a message entered into the message field;

use the general event descriptor and the patient identifier as an access key to access the patient database to obtain contextual information from the defined fields in the patient's chart, where the contextual information corresponds to the general event descriptor;

access the rules database and use the contextual information and the general event descriptor to identify a workflow being requested; and access the entity capability database and use the general event descriptor to identify at least one entity capable of providing the identified workflow corresponding to the general event descriptor and transmitting the message to the at least one entity that is capable of handling the workflow being requested by the user to begin the workflow.

12. The system of claim 11, wherein the electronic message template further comprises an attachment field configured to receive attached documents.

13. The system of claim 11, wherein the electronic message template further comprises a field for identifying the requester of the workflow.

14. The system of claim 11, further comprising the step of adding at least some of the contextual information to the message field in the electronic message.

15. The system of claim 14, further comprising the step of highlighting the contextual information added to the message field from the patient chart.

16. The system of claim 11, further comprising the step of providing a confirmation tool adapted to receive a manual confirmation prior to transmitting the electronic message to the at least one entity to initiate the workflow.

17. The system of claim 11, further comprising the step of highlighting the identified entity and providing a drop down menu to select an alternative entity identified as capable of providing the workflow.

18. The system of claim 11, further comprising a database storing a format for the electronic message to the at least one entity.

19. The system of claim 11, wherein the target field is configured to receive a second general event descriptor to provide a notification message to a second entity.

20. The system of claim 11, further comprising a confirmation tool selectable via the interface to confirm that the workflow is being requested.

* * * * *